United States Patent
Tremblay

(10) Patent No.: US 12,036,313 B2
(45) Date of Patent: *Jul. 16, 2024

(54) PERSONAL LUBRICANTS COMPRISING LAMBDA-CARRAGEENAN

(71) Applicant: LANVIRA, LLC, New York, NY (US)

(72) Inventor: Mario Elmen Tremblay, St. Petersburg, FL (US)

(73) Assignee: LANVIRA, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/085,720

(22) Filed: Dec. 21, 2022

(65) Prior Publication Data
US 2023/0121629 A1  Apr. 20, 2023

Related U.S. Application Data

(63) Continuation of application No. 18/011,796, filed as application No. PCT/US2020/038991 on Jun. 22, (Continued)

(51) Int. Cl.
*A61K 9/00* (2006.01)
*A61K 36/04* (2006.01)
(Continued)

(52) U.S. Cl.
CPC .......... *A61K 9/0034* (2013.01); *A61K 9/0014* (2013.01); *A61K 36/04* (2013.01); *A61K 47/10* (2013.01); *A61P 31/20* (2018.01)

(58) Field of Classification Search
CPC .... A61K 9/0034; A61K 9/0014; A61K 36/04; A61K 47/10; A61P 31/20
See application file for complete search history.

(56) References Cited

U.S. PATENT DOCUMENTS 3,907,770 A * 9/1975 Strong ................ C08B 37/0042
536/114
5,208,031 A 5/1993 Kelly
(Continued)

FOREIGN PATENT DOCUMENTS

WO  2008147049 A1  12/2008
WO  2009095639 A2   8/2009
(Continued)

OTHER PUBLICATIONS

Volery, et al., "Characterization of Commercial Carrageenans by Fourier Transform Infrared Spectroscopy Using Single-Reflection Attenuated Total Reflection", 2004, J. Agric. Food Chem., vol. 52, pp. 7457-7463 (7 pages).
(Continued)

*Primary Examiner* — Jianfeng Song
(74) *Attorney, Agent, or Firm* — Rankin, Hill & Clark LLP

(57) ABSTRACT

A pourable, non-toxic lubricating composition containing lambda carrageenan as an antiviral agent, for protection from viruses, including but not limited to sexually-transmitted viruses and respiratory viruses, and methods of using the lubricating compositions as a non-oily, pseudoplastic lubrication product and administering the carrageenan for reducing the propagation of sexually-transmitted viruses, including HPV, during sexual activity.

20 Claims, 2 Drawing Sheets

Related U.S. Application Data 2020, which is a continuation-in-part of application No. PCT/US2019/031429, filed on May 9, 2019, said application No. PCT/US2020/038991 is a continuation-in-part of application No. 16/391,653, filed on Apr. 23, 2019, now Pat. No. 10,688,043, which is a continuation-in-part of application No. 16/359,168, filed on Mar. 20, 2019, now abandoned, application No. 18/085,720, filed on Dec. 21, 2022 is a continuation of application No. 16/908,260, filed on Jun. 22, 2020, now Pat. No. 11,744,796, which is a continuation of application No. 16/391,653, filed on Apr. 23, 2019, now Pat. No. 10,688,043, said application No. 18/011,796 is a continuation of application No. 16/908,260, filed on Jun. 22, 2020, now Pat. No. 11,744,796, which is a continuation-in-part of application No. PCT/US2019/031429, filed on May 9, 2019, application No. 18/085,720, filed on Dec. 21, 2022 is a continuation of application No. PCT/US2020/038991, filed on Jun. 22, 2020, which is a continuation-in-part of application No. 16/391,653, filed on Apr. 23, 2019, now Pat. No. 10,688,043.

(60) Provisional application No. 62/669,532, filed on May 10, 2018, provisional application No. 62/645,347, filed on Mar. 20, 2018, provisional application No. 62/669,478, filed on May 10, 2018.

(51) Int. Cl.
    *A61K 47/10*     (2017.01)
    *A61P 31/20*     (2006.01)

(56) References Cited

U.S. PATENT DOCUMENTS

| | | | |
|---|---|---|---|
| 5,878,747 | A | 3/1999 | Enomoto et al. |
| 6,139,848 | A | 10/2000 | Ahmad et al. |
| 6,983,751 | B2 | 1/2006 | Osterberg |
| D599,486 | S | 9/2009 | Stewart |
| 8,367,098 | B2 | 2/2013 | Maguire et al. |
| 9,119,763 | B1 | 9/2015 | Leary |
| 10,688,043 | B1 | 6/2020 | Tremblay |
| 11,446,240 | B2 | 9/2022 | Tremblay |
| 2004/0112769 | A1* | 6/2004 | Perry .................. B65D 77/245 206/219 |
| 2005/0171053 | A1 | 8/2005 | Blakemore et al. |
| 2005/0239742 | A1 | 10/2005 | Place et al. |
| 2005/0261240 | A1 | 11/2005 | Maguire et al. |
| 2006/0127340 | A1 | 6/2006 | Roman et al. |
| 2006/0178602 | A1 | 8/2006 | Teng et al. |
| 2008/0227749 | A1 | 9/2008 | Place et al. |
| 2009/0088405 | A1 | 4/2009 | Kehoe et al. |
| 2009/0185995 | A1 | 7/2009 | Vochecowicz et al. |
| 2010/0012132 | A1 | 1/2010 | Harrison et al. |
| 2011/0015481 | A1 | 1/2011 | Scala |
| 2011/0229446 | A1* | 9/2011 | Roman .................. A61K 47/36 514/54 |
| 2014/0326250 | A1 | 11/2014 | Arnold et al. |
| 2015/0030748 | A1 | 1/2015 | Schultz et al. |
| 2015/0246065 | A1 | 9/2015 | Malhotra et al. |
| 2015/0313912 | A1 | 11/2015 | Karandikar |
| 2017/0360728 | A1 | 12/2017 | Strgar |
| 2018/0369137 | A1 | 12/2018 | Nguyen et al. |

FOREIGN PATENT DOCUMENTS

| | | | |
|---|---|---|---|
| WO | WO-2009095639 A2 * | 8/2009 | ............... A61K 8/73 |
| WO | 2013013172 A1 | 1/2013 | |
| WO | 2019002929 A2 | 1/2019 | |
| WO | 2019217618 A1 | 11/2019 | |

OTHER PUBLICATIONS

Anderson, "Techniques of Water-Resources Investigations Reports", Book 9, Chapter A6, Section 6.7 (Turbidity), Sep. 2005, U.S. Geological Survey, version 2.1 (55 pages).
Buck et al., "Carrageenan is a potent inhibitor of Papillomavirus infection", Jul. 2006, PLoS Pathogens vol. 2 No. 7, p. 671-680 (10 pages).
Roberts, et al., "Genital Transmission of HPV in a mouse model is potentiated by nonoxynol-9 and inhibited by carrageenan", Jul. 2007, Nature Medicine, vol. 13, No. 7, pp. 857-861 (5 pages).
Begay, et al., "Identification of Personal Lubricants that can Cause Rectal Epithelial Cell Damage and Enhance HIV Type 1 Replication in Vitro", 2011, AIDS Research and Human Retroviruses, vol. 27, No. 9, pp. 1019-1024 (6 pages).
"Use and procurement of additional lubricants for male and female condoms: WHO/UNFPA/FHI360—Advisory Note", 2012, World Health Organization Department of Reproductive Health and Research, WHO/RHR/12.33 (8 pages).
Araujo, et al., "Selective sulfation of carrageenans and the influence of sulfate regiochemistry on anticoagulant properties", 2012, Carbohydrate Polymers, vol. 91, pp. 483-491 (9 pages).
Necas, et al., "Carrageenan: A Review", 2013, Veterinari Medicina, vol. 58, No. 4, pp. 187-205 (19 pages).
Rodruiguez et al., "In vitro and in vivo evaluation of two carrageenan-based formulations to prevent HPV acquisition", Jun. 5, 2014, Antiviral Research vol. 108, p. 88-93 (6 pages).
"Compendium of Food Additive Specifications", 2014, Joint FAO/WHO Expert Committee on Food Additives, 79th Meeting, FAO JECFA Monographs 16 (93 pages, Relevant portion pp. 14-19).
Novestky, et al., "In vitro inhibition of human papillomavirus following use of a carrageenan-containing vaginal gel", 2016, Gynecologic Oncology, vol. 143, pp. 313-318 (6 pages).
Diez F, et al., "Development of an Analytical Method to Determine the Amount of ê Carrageenan in HPMC Capsules by LCMS", obtained May 3, 2018 from http://abstracts.aaps.org/Verify/AAPS2017/PosterSubmissions/M8109.pdf, American Association of Pharmaceutical Scientists (1 page).
"<785> Osmolality and Osmolarity", Dec. 2017, United States Pharmacopeial Convention (USP)—Physical Tests (3 pages).
"Carrageenan Info: Technical Information", obtained Apr. 11, 2018, MCPI Corporation, http://www.mcpicarrageenan.com/tech.html#Viscosity (8 pages).
Magnan, et al., "Efficacy of a Carrageenan gel Against Transmission of Cervical HPV (CATCH): Interim Analysis of a randomized, double-blind, placebo-controlled, phase 2B trial", Apr. 2018, Clin Microbiol Infect, vol. 25, No. 2, abstract only (2 pages).
Tremblay, "Declaration of Mario Elmen Tremblay", Nov. 13, 2019 (4 pages).
International Search Report and Written Opinion dated Oct. 22, 2019 for related International Application No. PCT/US2019/031429, filed May 9, 2019 (14 pages).
International Search Report and Written Opinion dated Jan. 14, 2021 for corresponding International Application No. PCT/US2020/038991, filed Jun. 22, 2020 (7 pages).
Non-final Office Action dated Jul. 1, 2019 in related U.S. Appl. No. 16/391,653, filed Apr. 23, 2019 (15 pages).
Final Office Action dated Sep. 27, 2019 in related U.S. Appl. No. 16/391,653, filed Apr. 23, 2019 (18 pages).
Non-final Office Action dated Nov. 10, 2020 in related U.S. Appl. No. 16/908,260, filed Jun. 22, 2020 (16 pages).
Final Office Action dated Apr. 1, 2021 in related U.S. Appl. No. 16/908,260, filed Jun. 22, 2020 (29 pages).
Non-final Office Action dated Oct. 18, 2021 in related U.S. Appl. No. 16/908,260, filed Jun. 22, 2020 (26 pages).
Final Office Action dated Jun. 23, 2022 in related U.S. Appl. No. 16/908,260, filed Jun. 22, 2020 (20 pages).
Non-final Office Action dated Dec. 27, 2021 in related U.S. Appl. No. 16/908,276, filed Jun. 22, 2020 (18 pages).

(56) References Cited

OTHER PUBLICATIONS

Final Office Action dated Jun. 22, 2022 in related U.S. Appl. No. 16/908,276, filed Jun. 22, 2020 (18 pages).

* cited by examiner

PERSONAL LUBRICANTS COMPRISING LAMBDA-CARRAGEENAN

CROSS-REFERENCE TO RELATED APPLICATIONS

The present application is a continuation of U.S. application Ser. No. 18/011,796 filed Dec. 20, 2022, which is a national stage entry of International Application No. PCT/US2020/038991 filed Jun. 22, 2020, which (1) is a continuation-in-part of International Application No. PCT/US2019/031429 filed on May 9, 2019, which claims the benefit of U.S. Provisional Application No. 62/669,532 filed on May 10, 2018, and (2) is a continuation-in-part of U.S. application Ser. No. 16/391,653 filed on Apr. 23, 2019, now U.S. Pat. No. 10,688,043, which is a continuation-in-part of U.S. application Ser. No. 16/359,168 filed on Mar. 20, 2019, which claims the benefit of U.S. Provisional Application No. 62/645,347 filed on Mar. 20, 2018. The present application is also a continuation of U.S. application Ser. No. 16/908,260 filed on Jun. 22, 2020. U.S. application Ser. No. 18/011,796 is also a continuation of U.S. application Ser. No. 16/908,260 filed on Jun. 22, 2020. All of the preceding applications are hereby incorporated by reference in their entireties.

FIELD OF THE INVENTION

The present invention relates to processes for making personal lubricant compositions useful for reducing or inhibiting the transmission of human papillomavirus among partners during sexual activity.

BACKGROUND OF THE INVENTION

According to the World Health Organization (WHO), human papillomavirus (HPV) is the most common sexually transmitted infection (STI) in the world, with over 14 million people acquiring new infections annually. In the United States alone, more than 42% of the people between the ages of 18 and 59 are infected with HPV, and 1 out of every 9 men are infected with oral HPV. Additionally, HPV is the root cause of essentially all cervical cancers, the second most common cancer in women worldwide by age-standardized incidence rate, leading to approximately 500,000 deaths per year. More than 85% of cervical cancer deaths are in developing countries, where it accounts for 13% of all female cancers. WHO also estimates that HPV causes 90% of anal cancer. In a separate study on HPV and throat cancer, AECOM found that the presence of an HPV type in the mouth increases the odds of developing head and neck cancer by twenty-two times. HPV is also the underlying cause of all genital warts.

HPV is spread from skin-to-skin contact, most commonly transmitted during sexual activity to the genitals, anus, and mouth. Consequently, condoms are only marginally effective in preventing transmission of HPV. While there are some treatment options for HPV, the reality is that there are more than 150 strains of HPV, approximately 30 of which have been shown to cause cancers and genital warts. Vaccines have been developed and can be useful—however, the best HPV vaccine available in the United States today only provides antiviral activity against 9 of the more than 150 HPV strains and they are only efficacious for a small subset of people. In 2015, the CDC reported that HPV vaccines only have an uptake rate 40% among adolescents, and that they are generally ineffective for people over 26 years old, as well as African-American women of any age. Further, the CDC has also reported that vaccines are also ineffective if the person has previously been exposed to HPV. Additionally, HPV vaccines are typically expensive, require multiple treatments or injections, and are largely unavailable to people in developing countries. As a result, a large proportion of people are unvaccinated and rely on condoms as their only protection against HPV.

There have been some promising studies about the use of carrageenan formulations, particularly formulations containing lambda-forms of carrageenan, to reduce or inhibit the transmission of a variety of viruses in vitro (see Buck, C. B., et al., (2006) *PLoS Pathogens* 2 (7):671-680) and in vivo in mice (see Roberts, J. N., et al., (2007) *Nature Medicine* 13 (7):857-861, and Maguire, R. A., et al., (1998) *Sexually Transmitted Diseases* 25 (9):494-500). Several other patents and patent publications similarly discuss the use of carrageenan within medicaments as an antimicrobial or antiviral compound (see U.S. Pat. Nos. 5,208,031 and 8,367,098, and U.S. Pat. Pubs. 2005/0171053, 2005/0239742, 2005/0261240, 2006/0127340, 2008/0227749, 2009/0088405, and 2011/0229446, the disclosures of which are incorporated by reference in their entireties).

More recently, in vivo studies in humans have shown that lambda-carrageenan formulations can be utilized to inhibit the transmission of HPV during sexual activity (see Magnan, S., et al., (2019) *Clin. Microbiol. Infect.* 25 (2):210-216, the disclosure of which is incorporated by reference in its entirety). Yet, there are very few commercially-available personal lubricants that contain carrageenan because the carrageenans are very difficult to process into a form that is suitable for use during sexual activity. Carrageenans are large, highly flexible polysaccharides that are almost exclusively obtained as complex mixtures of at least two, and typically three, different forms: kappa-carrageenan, iota-carrageenan, and lambda-carrageenan, which differ in their degree of sulfation. kappa- and iota-forms of carrageenan, which contain the fewest number of ester sulfate groups per molecule, predominate most carrageenan mixtures and are typically used in the food or cosmetic industries as gelling or thickening agents. On the other hand, lambda-carrageenan has the most ester sulfate groups per polysaccharide, and is unable to form a gel at all. Increased ester sulfate levels generally result in a lower solubility temperature in water, and go hand in hand with decreased gel strength or inhibition of gel formation, in the case of lambda-carrageenan. When present, all combinations of kappa-, iota-, and lambda-forms of carrageenan, as a function of total concentration of carrageenan in a composition, have an exponential effect on the composition's viscosity. This can cause a loss of rheological, tactile, and performance benefits when the composition is used as a sexual lubricant. In particular, carrageenan-based formulations are prone to drying quickly after being applied, resulting in sticky, non-lubricous residues that defeat the purpose of using a personal lubricant in the first place. Additionally, the viscosity of a particular carrageenan-containing composition is highly sensitive to the exact proportions of the kappa-, iota-, and lambda-forms within the composition. Thus, a composition that contains 50% lambda-carrageenan and 50% kappa-carrageenan will have a different viscosity than a composition that contains 70% lambda-carrageenan and 30% kappa-carrageenan, even where the total concentration of carrageenan in both compositions is identical. This effect is exacerbated in compositions that comprise all three forms of carrageenan. Consequently, the viscosity of carrageenan-containing compositions is generally not predictable from one composition to the next when the proportions of the kappa-, iota-, and lambda-forms are different, even when the total carrageenan concentration is the same.

Further, the processing steps themselves that are used to make carrageenan-containing compositions can have an effect on the viscosity and performance as a sexual lubricant. For instance, the temperature at which components are mixed has a dramatic effect on the viscosity of a carrageenan-containing product, particularly as a function of the ratio of each form of carrageenan within the mixture. When unprocessed carrageenan mixtures are placed in an aqueous-based solvent and heated, individual polysaccharides within the mixture begin to hydrate and intermolecularly interact with other polysaccharides, increasing the viscosity of the composition. As the temperature is increased further, intermolecular interactions are disrupted and the carrageenans homogenize and are contained within an aqueous solution phase, decreasing the overall viscosity to near starting levels. However, the proportions of each form of carrageenan that are contained within the composition can affect what happens upon cooling. When the predominant form is kappa- or iota-carrageenan, the cooled composition will form a gel, whereas when the predominant form is lambda-carrageenan, the cooled composition will not form a gel. Nonetheless, the relative proportions of kappa- and iota-carrageenan within the composition nonetheless affect the viscosity in lambda-carrageenan containing compositions that do not gel.

On the other hand, excessively heating carrageenan-containing compositions can have the effect of breaking intramolecular bonds within neighboring sugar units, effectively causing significant changes to the carrageenan molecules and reducing their average molecular weight. This can cause the viscosity of the resulting composition to decrease even further, but comes with a trade-off of causing the composition to dry out even more quickly once it is applied. Similarly, mixing carrageenan-containing mixtures for an extended period of time at high speed or under high-shear conditions can also disrupt intra- and intermolecular relationships of the carrageenan molecules within the composition.

Consequently, there remains a need for formulation that contains lambda-carrageenan and also performs satisfactorily as a sexual lubricant that allows both men and women to protect themselves from HPV transmission in a pleasant and unobtrusive fashion. The lubricant formulation must balance efficacy against HPV while retaining the viscosity, tactility, and performance enhancements gained by using personal lubricants during sexual activity. There also remains a need for a product that can be used in in conjunction with condoms or other sexual accessory devices that reduce the risk of transmitting HPV, HIV, and herpes during sexual activity, particularly in encounters involving two or more men.

SUMMARY OF THE INVENTION

The present invention provides processes for making low-viscosity, antiviral lubricous compositions that include lambda-carrageenan and are useful for reducing, inhibiting, or ameliorating the transmission, persistence, or symptoms caused by viruses, including but not limited to sexually-transmitted viruses and other disease-causing viruses from a taxonomic family can include any one of, and alternatively can be selected from the group consisting of, Orthomyxoviridae, paramyxoviridae, pneumoviridae, coronaviridae, retroviridae, herpesviridae, papillomaviridae, picornaviridae, reoviridae, and adenoviridae, and combinations thereof. The antiviral lubricous compositions made according to the disclosed processes can be applied to any epithelial or skin tissue which a virus can reside or be spread, including the tissue within or on the cervix, vulva, vagina, clitoris, penis, anus, mouth, nose, nasal cavity, or throat.

In various embodiments, antiviral lubricous compositions made by processes of the present invention can be used in conjunction with sexual activity. As used herein, the term "sexual activity" includes intimate or sexual contact with the skin or epithelial tissue within or on the cervix, vulva, vagina, clitoris, penis, anus, mouth, or throat of one, two, or more sexual partners. In some embodiments, the application of antiviral lubricous compositions of the present invention are effective in reducing the transmission of sexually-transmitted viruses in humans, non-limiting examples of which include human papilloma virus (HPV), human immunodeficiency virus (HIV), and herpes simplex virus (HSV), relative to placebo compositions that do not contain lambda-carrageenan. In further embodiments, the antiviral lubricous compositions provide protection against the transmission of HPV, including but not limited to HPV strains known to cause cancer, that can occur during male-female sexual encounters, male-male sexual encounters, and female-female sexual encounters. In even further embodiments, the antiviral lubricous compositions can provide protection against the transmission of HPV among high-risk sexual partners, including those who are already infected with at least one strain of HPV.

In various embodiments, any of the antiviral lubricous compositions described herein can be contacted with the skin or epithelial tissue, particularly skin or epithelial tissue located on or within at least one of the vagina, anus, mouth, or penis, of one or more of the sexual partners prior to sexual activity, in order to prophylactically inhibit the transmission of HPV from one sexual partner to another. In such embodiments, the antiviral lubricous composition can be contacted with the skin of one or more of the sexual partners less than 8 hours prior, for example, less than 4 hours, 2 hours, 1 hour, 30 minutes, 15 minutes, 5 minutes, 1 minute, or 30 seconds prior, to sexual activity, down to less than 1 second prior to sexual activity. In other embodiments, the antiviral lubricous composition can be contacted with the skin or epithelial tissue, particularly skin or epithelial tissue located on or within at least one of the vagina, anus, mouth, or penis, of one or more of the sexual partners after sexual activity, in order to reduce the spread of HPV from cell to cell after HPV has been transmitted. In such embodiments, the antiviral lubricous composition can be contacted with the skin or epithelial tissue of one or more of the sexual partners less than 8 hours after, for example, less than 4 hours, 2 hours, 1 hour, 30 minutes, 15 minutes, 5 minutes, 1 minute, or 30 seconds after, sexual activity, down to less than 1 second after sexual activity.

In various embodiments, antiviral lubricous compositions made by processes of the present invention can be applied to a person's skin or epithelial tissue independently of engaging in sexual activity. In some embodiments, the antiviral lubricous composition can be applied to reduce, inhibit, or ameliorate the transmission or effects of non-sexually transmitted viruses, including but not limited to coronaviruses, reoviruses, adenoviruses, orthomyxoviruses, paramyxoviruses, pneumoviruses, picornaviruses, and non-sexually transmitted retroviruses and herpes viruses. Non-limiting examples of diseases caused by such viruses include, but are not limited to severe acute respiratory disease (SARS), COVID-19, influenza, measles, mumps, varicella, enterovirus, rhinovirus, polio, adenovirus, and rotavirus. In some embodiments, the antiviral lubricous composition can be applied to animals having an infection from a disease caused by a virus caused by any of the viral families or types described above. Methods and substrates for applying an antiviral lubricous composition to help treat or reduce the effects of such conditions, in humans or animals, is described in further detail below.

In other embodiments, the antiviral lubricous compositions can be utilized in conjunction with feminine hygiene, for such purposes including but not limited to: as a vaginal moisturizer, as a vaginal deodorizer, and as a vaginal odor eliminator.

In another embodiment, the antiviral lubricous compositions are non-Newtonian, pseudoplastic fluids that undergo thixotropic shear thinning that reduces the composition's viscosity even further in response to mechanical strain. As a non-limiting example, such mechanical strain can occur when one, two, or more people engage in sexual activity, including sexual activity between male and female sexual partners, two or more male sexual partners, two or more female sexual partners, and combinations thereof.

In another embodiment, the antiviral lubricous compositions possess a rheological profile in which the lubricity of a dried antiviral lubricous composition on the skin can be retained upon adding water or other bodily fluids to the dried antiviral lubricous composition. Non-limiting examples of bodily fluids include saliva and vaginal secretions or discharge. In further embodiments, upon adding water or bodily fluids to a dried antiviral lubricous composition, the antiviral lubricous composition retains its antiviral activity, including against HPV.

In various embodiments, the antiviral lubricous compositions of the present invention can be prepared substantially free of components typically utilized in commercially-available personal lubricants, including but not limited to: oils, particularly silicone oils; cellulose; and polyquaterniums. In various embodiments, the antiviral lubricous compositions can be prepared to be substantially free of spermicides, such as nonoxynol-9, that are also often present commercially-available personal lubricants. However, in other embodiments, the antiviral lubricous compositions can be prepared to include oils, cellulose, polyquaterniums, and/or nonoxynol-9.

In another embodiment, processes to form antiviral lubricous compositions of the present invention can comprise the steps of: (a) providing a carrageenan powder comprising carrageenan, the carrageenan comprising at least 80% by weight lambda-carrageenan and up to 10% by weight of a secondary carrageenan selected from the group consisting of iota carrageenan and kappa-carrageenan, including combinations thereof, and preferably 10% by weight kappa-carrageenan; (b) combining, while mixing, the carrageenan powder with an aqueous solution comprising a quantity of a polyol, to form an aqueous carrageenan suspension; (c) heating the aqueous carrageenan suspension up to a temperature of at least 60° C.; (d) mixing for a time sufficient to transform the heated aqueous carrageenan suspension into an aqueous homogeneous solution; (e) cooling the aqueous homogeneous solution to a temperature of less than 50° C.; and (f) mixing one or more pH-adjusting agents into the cooled aqueous homogeneous solution, thereby forming the antiviral lubricous composition.

In various embodiments, the carrageenan suspension is turbid. When substantially all of the polysaccharides within the carrageenan suspension are homogenized upon heating and mixing, the carrageenan suspension clarifies and the resulting homogeneous solution is translucent. In another embodiment, the antiviral carrageenan suspension becomes and remains transparent upon formation of the homogeneous solution. In another embodiment, there are substantially zero particulates, aggregates, or agglomerates visible within the antiviral lubricous composition.

In various embodiments, the turbidity of any of the mixtures, suspensions, or antiviral lubricous compositions disclosed herein can be described quantitatively based on the method of determining the concentration of suspended particles in the sample, including but not limited to Formazin Nephelometric Units (FNU), Jackson Turbidity Units (JTU), and Nephelometric Turbidity Units (NTU). In another embodiment, the turbidity of any of the mixtures, suspensions, or antiviral lubricous compositions described herein are characterized as a function of NTU. In another embodiment, the turbidity of the carrageenan suspension upon the addition of carrageenan to the aqueous solution is at least 100 NTU, including at least 200, 300, 400, 500, 600, 700, 800, 900, 1000, 2000, or 3000 NTU, up to at least 4000 NTU. In another embodiment, the turbidity of the homogenized antiviral lubricous composition is less than 25 NTU, including less than 20, 15, 10, 8, 6, 5, 4, 3, or 2 NTU, down to less than 1 NTU, preferably less than or equal to 5 NTU, and more preferably approximately equal to the turbidity of drinking water.

In various embodiments, the step of combining while mixing the carrageenan powder with the aqueous solution comprises the sub-steps of (A): mixing the carrageenan powder with a polyol for a time sufficient to form a wet carrageenan mixture, and (B) combining, while mixing, the wet carrageenan mixture with an aqueous solution for a time sufficient to form the aqueous carrageenan suspension. In various embodiments, the weight ratio of the polyol to the carrageenan within the wet carrageenan mixture is at least 1:10, including at least 1:5, 1:1, 2:1, 4:1, 6:1, 8:1, 10:1, 20:1, 30:1, or 40:1, up to at least 50:1. In further embodiments, the weight ratio of the polyol to the carrageenan is 1:1 to 10:1. In various embodiments, the weight ratio of the aqueous solution mixed with the wet carrageenan mixture to form the carrageenan suspension is 3:1 to 60:1. In still further embodiments, the weight ratio of the aqueous solution mixed with the wet carrageenan mixture to form the carrageenan suspension is 8:1 to 45:1.

In various embodiments, the step of mixing the wet carrageenan mixture with the aqueous solution comprises dispersing the carrageenan contained in the wet carrageenan mixture within the aqueous solution. In a further embodiment, the step of dispersing comprises sufficient shear mixing of the carrageenan powder with the polyol with a dispersing mixer for a time sufficient to homogenize the carrageenan into the aqueous solution, while also minimizing the breaking of intramolecular bonds between sugar residues within each carrageenan polysaccharide.

In various embodiments, heating one or more of the wet carrageenan mixture, the aqueous carrageenan suspension, and/or the antiviral lubricous composition enables the solubilization and homogenization of the carrageenans in water. In various embodiments, one or more of the wet carrageenan mixture, the aqueous carrageenan suspension, and/or the antiviral lubricous composition is heated to a temperature of at least 60° C., for example, at least 65° C., 70° C., 75° C., 80° C., 85° C., or 90° C., and optionally up to at least 95° C. In various embodiments, the aqueous carrageenan suspension is heated to at least 70° C., and up to 75° C.

In various embodiments, a step of mixing of other powdered, solid, or liquid adjuvants into the aqueous solution comprises agitating the adjuvants within the aqueous solution under sufficient shear mixing and for a time sufficient to form a compositionally uniform solution.

In various embodiments, the carrageenan powder comprising lambda-carrageenan is a dried extract from sea algae, particularly from the red algae, *Chondrus crispus*. In various embodiments, lambda-carrageenan comprises at least 80%, for example, at least 85%, 90%, or 95% by weight of the sea algae extract. In various embodiments, lambda-carrageenan comprises up to 100%, for example, up to 95%, 90%, or 85%, by weight of the sea algae extract. In various embodiments, lambda-carrageenan comprises 90% by weight of the sea algae extract.

In various embodiments, the carrageenan powder consists of carrageenan in powder form. In another embodiment, the carrageenan powder consists essentially of carrageenan in powder form.

In various embodiments, the carrageenan powder can comprise carrageenan in powder form and an additional powder component. Non-limiting examples of an additional powder component includes a pH adjusting agent, a disinfectant, a preservative, a sweetener, and a salt, which are all described in further detail, below.

In various embodiments, within a carrageenan powder comprising lambda-carrageenan, the remaining carrageenan species can comprise kappa-carrageenan, iota-carrageenan, or a combination of kappa-carrageenan and iota-carrageenan. In various embodiments, either or both of kappa-carrageenan and iota-carrageenan can comprise up to 20% by weight of the carrageenan powder, for example, up to 15%, 10%, 8%, 6%, 4%, 2%, or 1%, by weight of the carrageenan powder. In various embodiments, when present, kappa-carrageenan and iota-carrageenan together comprise at least 1%, for example, 2%, 4%, 6%, 8%, or 10%, by weight, and up to at least 15% by weight of the carrageenan powder. In various embodiments, lambda-carrageenan can comprise 90% by weight of the carrageenan powder, and kappa-carrageenan and iota-carrageenan together comprise 10% by weight of the carrageenan powder. In various embodiments, lambda-carrageenan can comprise 90% by weight of the carrageenan powder, and kappa-carrageenan comprises 10% of the carrageenan powder. In various embodiments, lambda-carrageenan can comprise 90% by weight of the carrageenan powder, and lambda-carrageenan comprises 10% of the carrageenan powder.

In various embodiments, antiviral lubricious composition comprises, by weight, at least 0.001% carrageenan, for example, at least 0.01, 0.1, 0.5, 0.75, 1.0, 1.2, 1.4, 1.6, 1.8, 2.0, 2.2, 2.4, 2.5, or 3%, carrageenan, and optionally up to at least 5% carrageenan. In other embodiments, the antiviral lubricious composition comprises less than 5% by weight carrageenan, for example, less than 3, 2.5, 2.4, 2.2, 2, 1.8, 1.6, 1.4, 1.2, 1.0, 0.75, 0.5, 0.1, 0.01, or 0.001%, by weight. In further embodiments, the antiviral lubricious composition comprises 0.2% to 2.3% by weight carrageenan. In even further embodiments, the antiviral lubricous composition comprises 0.8% by weight to 2% by weight carrageenan. In still further embodiments, the antiviral lubricous composition comprises 1.5% to 1.7% by weight carrageenan.

In various embodiments, the addition of one or more polyols to the carrageenan powder causes the carrageenan polysaccharides within the powder to partially unwind, making additional polarizable contacts available to interact upon addition of the aqueous solution. In other embodiments, the presence of polyols within the antiviral lubricous composition enhances the sensation, tactility, and/or lubricity experienced by the wearer or his or her partners during sexual activity. In further embodiments, the at least one polyol can be selected from the group consisting of: glycerol; propylene glycol (1,2-propanediol); 1,3-propanediol; 1,3-butanediol; 1,4-butanediol; 2,3-butanediol; xylitol; sorbitol; erythritol; isomalt; lactitol; maltitol; mannitol; polyethylene glycol; and polypropylene glycol; including combinations thereof. In even further embodiments, the antiviral lubricous composition comprises less than 50% by weight polyol, for example, less than 25, 15, 10, 9, 8, 7, 6, 5, 4, 3, 2, 1, 0.5, or 0.1% by weight of the antiviral lubricous composition. In other embodiments, the antiviral lubricous composition comprises at least 0.1% by weight of polyol, for example, at least 0.5, 1, 2, 3, 4, 5, 6, 7, 8, 9, 10, 15, 25, or 35% by weight of the polyol. In still further embodiments, the antiviral lubricous composition comprises less than 10% by weight polyol. In even still further embodiments, the antiviral lubricous composition comprises 0.5% to 5% by weight of the polyol. In other even still further embodiments, the antiviral lubricous composition comprises 4% to 4.5% by weight of the polyol. In some embodiments, the polyol is propylene glycol. In some embodiments, the polyol is 1,3-propanediol.

In various embodiments, the antiviral lubricous composition is a pourable composition that has a viscosity of less than 10,000 cP, for example, less than 8,000, 6,000, 5,000, 4,000, 3,000, 2,000 or 1,000 cP. In other embodiments, the antiviral lubricous composition has a viscosity of at least 500 cP, for example, at least 1,000, 2,000, 3,000, 4,000, 5,000, 6,0000 cP, or 8,000 cP. In further embodiments, the antiviral lubricous composition has a viscosity between 500 cP and 8,000 cP, more particularly between 1,000 cP and 4,000 cP, even more particularly between 2,000 cP and 3,000 cP. In some embodiments, the antiviral lubricous composition has a viscosity between 1,500 cP and 2,500 cP. In some embodiments, the antiviral lubricous composition has a viscosity of 2,000 cP.

In various embodiments, the antiviral lubricous composition has a viscosity that enables it to be poured from an open container, yet remains on a sloped, slanted, curved, or inverted surface upon application. Non-limiting examples of surfaces include skin or epithelial tissue such as the cervix, vulva, vagina, clitoris, penis, anus, nose, nasal cavity, mouth, and throat. Other non-limiting examples of surfaces to which an antiviral lubricous composition can be applied can include sexual accessories or devices such as sex toys, vibrators, rings, or beads, or internal applicators such as swabs, elongate stick or rods, wearable inserts, injectors, syringes, cannulas, or pipettes.

In various embodiments, upon exerting one or more shearing forces to or using the surface containing the applied antiviral lubricous composition, as is commonly applied during sexual activity, the viscosity of the antiviral lubricous composition decreases in a non-Newtonian manner. In further embodiments, the viscosity reduces to less than 5,000 cP, for example, less than 4,000, 3,000, 2,500, 2,000, 1,500, 1,000, 800, 600, 500, 400, or 300 cP, and optionally less than 200 cP. In other embodiments, the lubricity of the antiviral lubricous composition is retained upon exerting the shearing forces continuously for at least 15 seconds, for example, at least 30 seconds, 1 minute, 2 minutes, 3 minutes, 4 minutes, 5 minutes, 10 minutes, 15 minutes, 20 minutes, 30 minutes, or 45 minutes, and optionally up to at least one hour.

In various embodiments, increasing the total concentration of carrageenan within the antiviral lubricous composition has an exponential increase on the composition's viscosity. In further embodiments, the relative concentration of the kappa-, iota-, and lambda-forms of carrageenan differentially affect the rate of exponential growth of the viscosity of the antiviral lubricous composition. In even further embodiments, the antiviral lubricous composition comprises 90% lambda-carrageenan and 10% of one or both of kappa-carrageenan or iota-carrageenan. In even still further embodiments, the antiviral lubricous composition comprises 90% of lambda-carrageenan and 10% of kappa-carrageenan. In even still further embodiments, the antiviral lubricous composition comprises 90% of lambda-carrageenan and 10% of iota-carrageenan.

In various embodiments, the mixing rotor type and mixing speed can be optimized to control the viscosity of the resulting antiviral lubricous composition. In some embodiments, mixing can be conducted under shear conditions sufficient to homogenize the carrageenan-containing composition while preserving the length of each carrageenan polysaccharide and maintaining their lubricity prior to applying the composition to the skin or epithelial tissue, particularly before or in conjunction with sexual activity.

In various embodiments, a device for performing a mixing step of the present invention, including a step of agitating or a step of dispersing, can comprise any conventional mixing apparatus for the intended use. One non-limiting example of a mixing apparatus is a paddle mixer. One example of a paddle mixer is a mixer that comprises at least one folding impeller blade. One specific example of a paddle mixer is a Mixer Direct R-AD665 industrial gallon paddle mixer with two folding impeller blades. In even further embodiments, a paddle mixer is used for each of the mixing steps for forming the antiviral lubricous composition. In other even further embodiments, each of the mixing steps is conducted with low-speed mixer operating at a rotational speed of equal or less than 500 revolutions per minute (RPM). In still further embodiments, mixing of the antiviral lubricous composition after homogenizing the carrageenan within the aqueous solution can occur at speeds less than or equal to 250 RPM.

In various embodiments, an antiviral lubricous composition formed by a process of the present invention has an osmolality that enables skin or epithelial tissue, particularly epithelial tissue within the vagina or rectum, to maintain a healthy plasma water-electrolyte balance. In further embodiments, the osmolality of the antiviral lubricous compositions is less than 1200 mOsmol/kg, for example, less than 1000, 900, 800, 700, 600, 500, 400, 300, or 200 mOsmol/kg, and optionally, less than 100 mOsmol/kg. In even further embodiments, the osmolality of the antiviral lubricous composition is 650 mOsmol/kg to 800 mOsmol/kg. In other even further embodiments, the osmolality of the antiviral lubricous composition is isosmolal with the normal osmolality of human semen, between 250 mOsmol/kg and 380 mOsmol/kg. In still further embodiments, the osmolality of the antiviral lubricous composition is isosmolal with the normal osmolality of vaginal secretions, between 260 mOsmol and 290 mOsmol/kg.

In various embodiments, antiviral lubricous compositions of the present invention can further comprise one or more pH-adjusting agents comprising an acid, particularly an organic acid, and more particularly citric acid. In other embodiments, the one or more pH-adjusting agents can include a weak acid and its conjugate base to create a buffer. In one non-limiting example, the addition of citrate to the antiviral lubricous composition can be accomplished by adding both citric acid and a citrate salt, such as sodium or magnesium citrate.

In various embodiments, the pH of the antiviral lubricous composition is less than 9.0, for example, less than 8.0, 7.0, 6.5, 6.0, 5.5, 5.0, 4.5, or 4.0, and optionally less than 3.5. In other further embodiments, the pH of the antiviral lubricous composition is at least 3.5, for example, at least 4.0, 4.5, 5.0, 5.5, 6.0, 6.5, 7.0 or 8.0, and optionally, at least 9.0. In even further embodiments, the pH of the antiviral lubricous composition is between 5.5 and 7.0. In still further embodiments, the pH of the antiviral lubricous composition can be optimized to be either applied to the vagina directly, or to contact the vagina during sexual activity. In such embodiments, the pH of the antiviral lubricous composition is between 3.5 and 5.5, particularly 4.5.

In various embodiments, the pH of the antiviral lubricous composition is adjusted after the carrageenan has been homogenized and the resulting antiviral lubricous composition has been cooled. In further embodiments, the antiviral lubricous composition can be cooled to less than 50° C., for example, less than 45° C., 40° C., 35° C., 30° C., or 25° C., and optionally, less than 20° C. In even further embodiments, the antiviral lubricous composition is cooled to less than 30° C. before the pH of the composition is adjusted.

In various embodiments, the concentration of the one or more pH-adjusting agents within the pH-adjusted antiviral lubricous composition is less than 1% by weight of the antiviral lubricous composition, for example, less than 0.5%, 0.25%, 0.1%, or 0.05%, and optionally, less than 0.01% by weight of the antiviral lubricous composition. In further embodiments, the concentration of the one or more pH-adjusting agents within the pH-adjusted antiviral lubricous composition is equal or less than 0.1% by weight. In even further embodiments, the weight of the one or more pH-adjusting agents within the pH-adjusted antiviral lubricous composition is equal or less than 0.05% by weight. The pH-adjusting agents can be added into the composition as a component of the carrageenan powder to which the polyol is added, into the carrageenan suspension, or into the antiviral lubricous composition after the carrageenan is homogenized.

In various embodiments, processes for forming the antiviral lubricous composition can further comprise the step of mixing one or more sweeteners and/or one or more preservatives into either the carrageenan powder, the aqueous carrageenan suspension, or the cooled aqueous homogenous solution. In various embodiments, one or more sweeteners are added to the aqueous carrageenan suspension. In various embodiments, one or more preservatives are added along with the one or more pH-adjusting agents to the aqueous homogeneous solution. In various embodiments, each of the additional components, such as the sweeteners and preservatives described above, as well as salts and/or aromatic agents, can be included within the antiviral lubricant composition to supplement its antiviral activity, aid in application to skin or epithelial tissue, and/or enhance its performance during sexual activity.

In various embodiments, an antiviral lubricous composition of the present invention can further comprise one or more sweeteners, particularly saccharin, comprising 0.01% by weight to 1% by weight of the antiviral lubricous composition, particularly 0.1% to 0.5% by weight of the antiviral lubricous composition. In another embodiment, the concentration of saccharin in the antiviral lubricous composition is up to 0.5% by weight. In another embodiment, the concentration of saccharin in the antiviral lubricous composition is 0.125% by weight.

In various embodiments, saccharin can be added to the carrageenan mixture or the carrageenan suspension as an aliquot from a concentrated stock solution. In further embodiments, the total weight of the saccharin stock solution added to the carrageenan mixture or the antiviral lubricous composition comprises 1% to 10% by weight of the completed antiviral lubricous composition. In even further embodiments, the saccharin stock solution is a 2.5% by weight of saccharin in water. In still further embodiments, the amount of 2.5% by weight saccharin stock solution added to the carrageenan mixture is equal to 5% by weight of the antiviral lubricous composition, wherein the final concentration of saccharin in the antiviral lubricous composition is 0.125% by weight. In even still further embodiments, the saccharin is provided as sodium saccharin.

In various embodiments, an antiviral lubricous composition of the present invention can further comprise 0.01% to 1.0% by weight of one or more preservatives, particularly one or more preservatives selected from the group consisting of 2-phenoxylethanol, chlorphenesin, and sodium dehydroacetate, including combinations thereof.

In various embodiments, the antiviral lubricous compositions of the present invention can optionally further comprise one or more aromatic agents designed to provide a pleasing fragrant effect on the composition. Aromatic agents can include essential oils or component compounds within essential oils capable of imparting an odor. Non-limiting examples of fragrances that can be provided by such aromatic agents include citrus, lemon, berry, or peppermint fragrances. In some embodiments, aromatic agents can comprise between 0.01% and 5% by weight of the antiviral lubricous composition, particularly between 0.1% and 2.5% by weight of the antiviral lubricous composition.

In various embodiments, the antiviral lubricous compositions of the present invention can further comprise a salt, particularly a sodium salt or a zinc salt, more particularly a zinc salt, that can be utilized to increase the ionic strength of the composition while also supporting or complementing either or both of the rheological properties or antiviral activity of the composition. The salt can be added into the composition as a component of the carrageenan powder to which the polyol is added, into the carrageenan suspension, or into the antiviral lubricous composition after the carrageenan is homogenized.

In various embodiments, processes to form homogenized antiviral lubricous compositions of the present invention can be completed in less than 12 hours, for example, less than 10, 8, 6, 4, or 3 hours, and optionally, less than 2.5 hours. In further embodiments, processes to form homogenized antiviral lubricous compositions of the present invention are completed in 2 to 3 hours.

In another embodiment, a method for forming an antiviral lubricous composition can comprise the steps of: (a) providing a carrageenan powder comprising carrageenan, the carrageenan comprising 90% by weight lambda-carrageenan and 10% by weight kappa-carrageenan; (b) combining, while mixing, the carrageenan powder with an aqueous solution comprising propylene glycol, to form an aqueous carrageenan suspension; (c) adding one or more sweeteners to the aqueous carrageenan suspension; (d) heating the aqueous carrageenan suspension up to a temperature of at least 70° C. and up to 75° C.; (e) mixing the heated aqueous carrageenan suspension for a time sufficient to form an aqueous homogenous solution; (f) cooling the aqueous homogeneous solution to a temperature of less than 30° C.; and (g) mixing one or more pH-adjusting agents and one or more preservatives into the cooled aqueous homogeneous solution, sufficient to adjust the antiviral lubricous composition to a pH of 3.5 to 7.0, thereby forming an antiviral lubricous composition. In another embodiment, an antiviral lubricous composition formed by the above process can consist essentially of: 1.5% to 1.7% by weight of carrageenan, 4.0% to 4.5% by weight of propylene glycol, up to 0.5% by weight of the one or more sweeteners, up to 1% by weight of the one or more preservatives, and 0.01% to 1% by weight of one or more pH-adjusting agents, the balance water. In further embodiments, an antiviral lubricous composition formed by the above process can be translucent, have a viscosity of at least 2,000 cP, up to 3,000 cP, and a turbidity that is less than or equal to 25 NTU, preferably 5 NTU. In even further embodiments, the antiviral lubricous composition formed by the above process can have an osmolality in a range from at least 650 mOsmol/kg, up to 850 mOsmol/kg. In still further embodiments, the pH of the antiviral lubricous composition formed by the above process is 3.5 to 5.5. In other still further embodiments, the pH of the antiviral lubricous composition formed by the above process is 5.5 to 7.0. In even still further embodiments, the antiviral lubricous composition formed by the above process is effective in reducing, inhibiting, or ameliorating the transmission of HPV. In other even still further embodiments, the antiviral lubricous composition formed by the above process is effective in reducing, inhibiting, or ameliorating the transmission of COVID-19.

In another embodiment, the processes to form antiviral lubricous compositions of the present invention can comprise the steps of: (a) providing a carrageenan powder comprising carrageenan, the carrageenan comprising at least 90% by weight lambda-carrageenan and up to 10% by weight kappa-carrageenan; (b) mixing the carrageenan powder with a polyol, comprising agitating or stirring the carrageenan powder with the polyol for a time sufficient to form a wet carrageenan mixture, wherein the weight ratio of the glycol to the carrageenan is 1:1 to 10:1; (c) dispersing the wet carrageenan mixture into an aqueous solution under shear mixing for a time sufficient to form a turbid carrageenan suspension, wherein the weight ratio of the aqueous solution to the carrageenan is 45:1 to 8:1; (d) adding one or more sweeteners into the turbid carrageenan suspension, while agitating the turbid carrageenan suspension, wherein the sweetener comprises up to 0.5% by weight of the completed antiviral lubricous composition; (e) heating the turbid carrageenan suspension up to a temperature of 70° C. and under shear mixing for a time sufficient, including up to 100 minutes, to transform the turbid carrageenan suspension into a clarified homogeneous solution, thereby forming the antiviral lubricous composition; (f) cooling the homogenized antiviral lubricous composition until the temperature of the antiviral lubricous composition is less than 30° C.; (g) adding, under agitation, one or more pH-adjusting agents into the cooled antiviral lubricous composition, at a weight sufficient to adjust the antiviral lubricous composition to a pH of 3.5 to 7.0, and (h) adding, under agitation, one or more preservatives into the turbid carrageenan suspension or the cooled antiviral lubricous composition, at up to 1% by weight of the antiviral lubricous composition; wherein (i) the antiviral lubricous composition comprises 0.2% to 2.3% by weight carrageenan, and up to 10% by weight polyol; (ii) the antiviral lubricous composition has a viscosity of less than 5,000 cP; (iii) the antiviral lubricous composition is translucent; and (iv) the antiviral lubricous composition is effective in reducing, inhibiting, or ameliorating the transmission of human papillomavirus (HPV). In further embodiments, the antiviral lubricous composition comprises: 1.5% to 1.7% by weight of the carrageenan; 4% to 4.5% by weight of 1,2-propanediol; a viscosity of 2,000 cP to 3,000 cP; an osmolality of 650 mOsmol/kg to 850 mOsmol/kg; and a pH of 6.25 to 6.75. In even further embodiments, the carrageenan comprises 90% by weight lambda-carrageenan and about 10% by weight kappa-carrageenan. In even still further embodiments, the antiviral lubricous composition formed by the above process is effective in reducing, inhibiting, or ameliorating the transmission of HPV. In other even still further embodiments, the antiviral lubricous composition formed by the above process is effective in reducing, inhibiting, or ameliorating the transmission of COVID-19.

In another aspect, the present invention also describes methods for reducing, inhibiting, or ameliorating the transmission, symptoms, or effects of a viral infection, comprising the steps of: (a) providing any of the above-described antiviral lubricous compositions; and (b) contacting the antiviral lubricous composition with the skin or epithelial tissue of one or more of the partners. Non-limiting examples of skin or epithelial tissue to which the antiviral lubricous composition can be applied include the skin, cervix, vulva, vagina, clitoris, penis, anus, nose, nasal cavity, mouth, and throat. In another embodiment, the antiviral lubricous composition can be applied to any skin or epithelial tissue, either internal or external, in which a viral infection is known to be present.

In various embodiments, methods for reducing, inhibiting, or ameliorating the transmission, symptoms, or effects of a viral infection can comprise the steps of: (a) providing a substrate comprising one or more skin-contacting surfaces, wherein the substrate is configured for contacting skin or epithelial tissue and/or insertion into one or more body cavities; (b) lubricating one or more of the skin-contacting surfaces of the substrate with the antiviral lubricous composition, thereby producing a lubricated substrate; (c) contacting the lubricated substrate with the skin or epithelial tissue; and (d) transferring the antiviral lubricous composition from the lubricated substrate to the skin or epithelial tissue.

In various embodiments, methods for reducing, inhibiting, or ameliorating the transmission of a sexually-transmitted virus, including but not limited to HPV, HIV, and HSV, between two or more partners engaging in sexual activity can comprise the steps of: (a) providing any of the above-described antiviral lubricous compositions, and (b) contacting the antiviral lubricous composition with the skin or epithelial tissue of one or more of the partners, wherein the skin or epithelial tissue located on or within at least one of the vagina, anus, mouth, or penis. In further embodiments, at least one partner is male and at least one partner is female. In other further embodiments, at least two partners are male. In still other further embodiments, at least two partners are female. In yet other further embodiments, there are three or more sexual partners, comprising any combination of men or women.

In various embodiments, methods for reducing, inhibiting, ameliorating, or preventing the transmission of a sexually-transmitted virus, including but not limited to HPV, HIV, and HSV, between partners engaging in sexual activity can comprise the steps of: (a) providing a substrate comprising one or more skin-contacting surfaces, wherein the substrate is configured for insertion into one or more body cavities selected from the group consisting of the vagina, mouth, or anus; (b) lubricating one or more of the skin-contacting surfaces of the substrate with the antiviral lubricous composition, thereby producing a lubricated substrate; (c) contacting the lubricated substrate with the skin or epithelial tissue located on or within at least one of the vagina, anus, mouth, or penis of one or more of the partners; and (d) transferring the antiviral lubricous composition from the lubricated substrate to the skin or epithelial tissue.

In various embodiments, the substrate is a condom. In further embodiments, the condom comprises latex. In other further embodiments, the condom comprises polyurethane and/or other synthetic materials. In still other further embodiments, the condom is incompatible with oil-based personal lubricants. In yet still other further embodiments, the condom is selected from the group consisting of a male condom and a female condom.

In various embodiments in which a condom is a substrate, methods for reducing, inhibiting, ameliorating, or preventing the transmission of a sexually-transmitted virus, including but not limited to HPV, HIV, and HSV, between partners engaging in sexual activity further comprise the steps of: lubricating a skin-contacting surface of a condom; contacting the skin or epithelial tissue within mouth, vagina, or anus of one or more of the partners with the lubricated skin-contacting surface of the condom; and transferring the antiviral lubricous composition from the lubricated skin-contacting surface of the condom to the skin or epithelial tissue.

In various embodiments in which a condom is a substrate, methods for reducing, inhibiting, ameliorating, or preventing the transmission of a sexually-transmitted virus, including but not limited to HPV, HIV, and HSV, between partners engaging in sexual activity further comprise the steps of: placing a condom over the finger or penis of one partner; lubricating an external surface of the condom with the antiviral lubricous composition; contacting the skin or epithelial tissue within the mouth, vagina, or anus of one or more additional partners using the lubricated external surface of the condom; and transferring the antiviral lubricous composition from the lubricated external surface of the condom to the skin or epithelial tissue.

In various embodiments in which a condom is a substrate, methods for reducing, inhibiting, ameliorating, or preventing the transmission of a sexually-transmitted virus, including but not limited to HPV, HIV, and HSV, between partners engaging in sexual activity further comprise the steps of: lubricating the condom; sealing the lubricated condom within a packaging; storing the lubricated condom within the packaging; removing the lubricated condom from the packaging; applying the lubricated condom to the finger or penis of one of the sexual partners; contacting the skin or epithelial tissue within the mouth, vagina, or anus of one or more additional partners using the lubricated condom; and transferring the antiviral lubricous composition from the lubricated condom to the skin or epithelial tissue.

In various embodiments, the substrate is a sexual accessory device including but not limited to sex toys, dildos, vibrators, rings, or beads. In further embodiments, the method further comprises the steps of sealing the lubricated sexual accessory device within a packaging, storing the lubricated sexual accessory device within the packaging, and removing the lubricated sexual accessory device from the packaging prior to contacting the skin or epithelial tissue of one or more of the partners. The antiviral lubricous composition can be applied to any skin-contacting surface of the sexual accessory device, typically prior to contact with the skin of one or more the sexual partners, particularly prior to insertion into the vagina, anus, or mouth.

In various embodiments, a condom lubricated by any of the antiviral lubricous compositions of the present invention can be applied to an unlubricated sexual accessory device to provide lubricity for use during sexual activity. In other embodiments, an unlubricated condom can be applied to a sexual accessory device lubricated by any of the antiviral lubricous compositions of the present invention. In still other embodiments, an unlubricated condom can be applied to an unlubricated sexual accessory device and subsequently be lubricated by any of the antiviral lubricous compositions of the present invention.

In various embodiments, the substrate is an internal applicator configured for insertion into the vagina, rectum, mouth, or nose, and wherein the internal applicator is selected from the group consisting of a swab, an elongate stick or rod, a wearable insert, an injector, a syringe, a cannula, or a pipette. In further embodiments, the internal applicator comprises a skin-contacting surface that is configured to contact epithelial tissue within a person's body cavity, particularly within the vagina, nose, mouth, or rectum. In other further embodiments, the internal applicator comprises a container configured for housing or containing the antiviral lubricous composition prior to transferring the antiviral lubricous composition onto epithelial tissue within a person's body cavity, particularly the vagina, nose, mouth, or rectum.

In various embodiments, the substrate is a swab of sufficient length for insertion into the mouth or nose, to contact epithelial tissue within the nasal cavity or oral cavity, including the throat. In various embodiments, a lubricated swab can be inserted into the nose or mouth, to contact epithelial tissue within the nasal cavity or oral cavity, to reduce, inhibit, or ameliorate the transmission, symptoms, or effects of a viral respiratory infection, such as, as non-limiting examples, SARS, COVID-19, Middle East Respiratory Syndrome (MERS), and adenovirus.

The present invention also provides kits for reducing, inhibiting, or ameliorating the transmission of a sexually-transmitted virus, including but not limited to HPV, HIV, and HSV, between partners engaging in sexual activity, the kit comprising any of the above-described antiviral lubricous compositions and instructions describing any of the methods disclosed above for contacting the antiviral lubricous composition with the skin of one or more of the partners. The kit can further comprise any of the above-described substrates, including condoms, sexual accessory devices, and/or internal applicators.

These and other embodiments of the present invention will be apparent to one of ordinary skill in the art from the following detailed description.

DETAILED DESCRIPTION OF THE INVENTION

Figure 1:
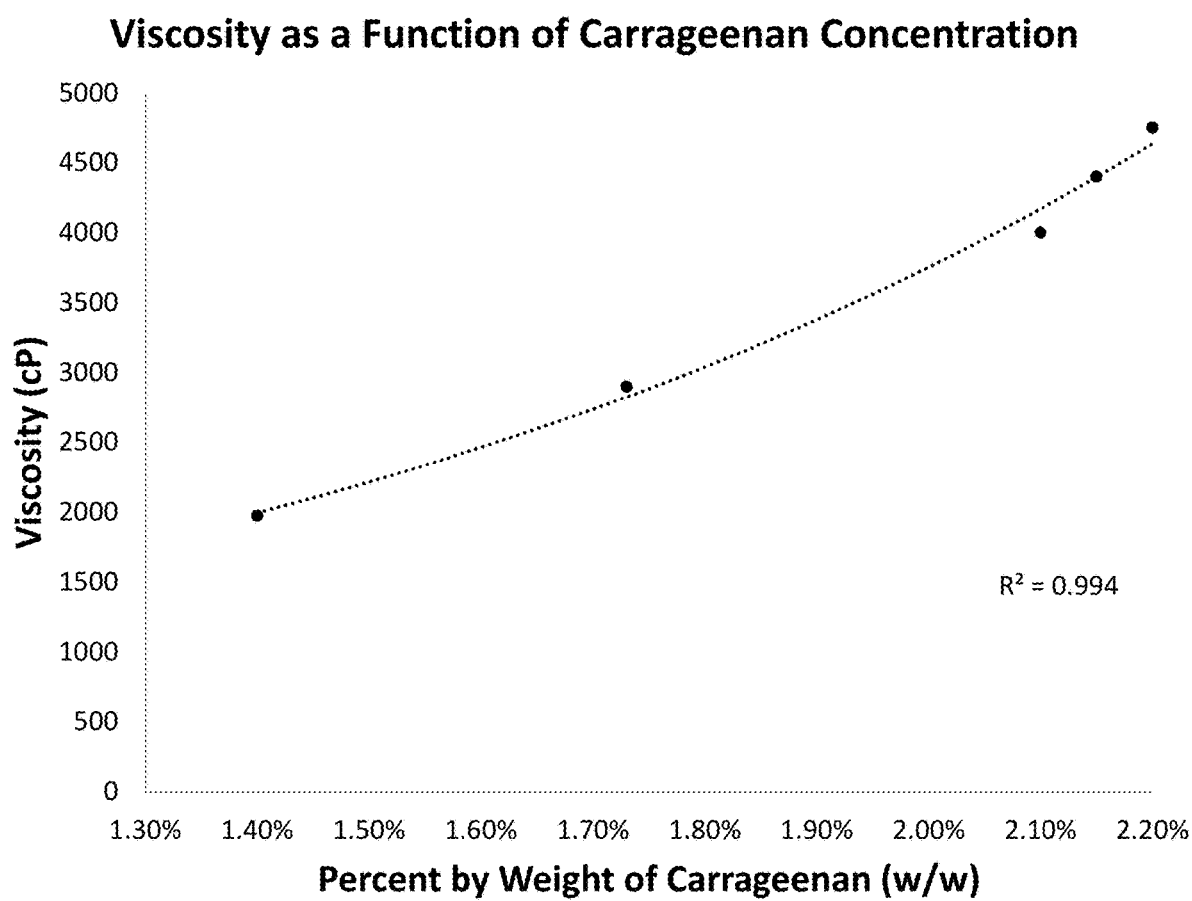
FIG. 1 shows a plot of the viscosity of antiviral lubricous compositions as a function of the concentration of carrageenan.

It should be understood that while reference is made to exemplary embodiments and specific language is used to describe them, no limitation of the scope of the invention is intended. Further modifications of the methods described herein, as well as additional applications of the principles of those inventions as described, which would occur to one skilled in the relevant art and having possession of this disclosure, are to be considered within the scope of this invention. Furthermore, unless defined otherwise, all technical and scientific terms used herein have the same meaning as commonly understood by one of ordinary skill in the art to which embodiments of this particular invention pertain. The terminology used is for the purpose of describing those embodiments only, and the terminology is not intended to be limiting unless specified as such. Headings are provided for convenience only and are not to be construed to limit the invention in any way. Additionally, throughout the specification and claims, a given chemical formula or name shall encompass all optical isomers and stereoisomers, as well as racemic mixtures where such isomers and mixtures exist.

The present disclosure includes aqueous compositions that have antiviral activity against several different taxonomic families, including but not limited to one or both of coronaviridae and papillomaviridae, and which can be utilized as personal lubricants during sexual activity. The antiviral lubricous compositions can be contacted with the skin or epithelial tissue anywhere a viral infection is known to be present either inside or outside the body, or in areas that are commonly lubricated during sexual activity, including but not limited to the cervix, vulva, vagina, clitoris, penis, anus, nose, nasal cavity, mouth, and throat. The antiviral lubricous compositions are capable of reducing, inhibiting, ameliorating, or preventing the transmission and/or the persistence of sexually-transmitted viruses, including human papillomavirus (HPV), human immunodeficiency virus (HIV), or herpes simplex virus (HSV) between sexual partners, including male-female, male-male, and female-female sexual partnerships.

Lambda-Carrageenan-Containing Compositions

The antiviral activity of the antiviral lubricous compositions of the present invention results from the presence of carrageenan, particularly lambda-carrageenan. Carrageenan is a generic term for a broad family of naturally occurring sulfated polysaccharides that are extracted from a wide range of species of seaweed algae, particularly from *Chondrus crispus*, a red seaweed found on the Atlantic coast of the United States. Extracted carrageenans can typically be obtained in one of ten forms, which differ in terms of sulfation content, sulfation location within each polysaccharide, and acid/base character. Three of the forms—kappa-carrageenan, iota-carrageenan, and lambda-carrageenan—are particularly common within compositions used in the food and pharmaceutical industries. The structures of kappa-carrageenan, iota-carrageenan, and lambda-carrageenan are shown below:

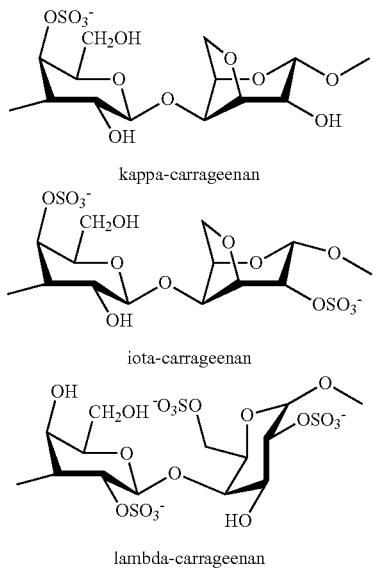

kappa-carrageenan iota-carrageenan lambda-carrageenan

As shown above, kappa-carrageenan, iota-carrageenan, and lambda-carrageenan comprise repeating galactose units. In particular, kappa-carrageenan and iota-carrageenan comprise alternating units of D-galactose and 3,6-anhydro-galactose (3,6-AG), whereas lambda-carrageenan does not comprise any 3,6-AG. Each form differs in the number of sulfate groups per disaccharide, where kappa-carrageenan, iota-carrageenan, and lambda-carrageenan comprise one, two, or three sulfate groups, respectively, per alternating unit. As the number of sulfate groups within the polysaccharides increase, the ability of particular forms of carrageenan to produce gels decreases. Similarly, all of the kappa-, iota-, and lambda-forms of carrageenan have the ability to solubilize in aqueous solution, although the temperature at which a particular form will solubilize is also a function of relative sulfate content. Thus, a pure sample of lambda-carrageenan can be solubilized within water at a lower temperature than a pure sample of kappa-carrageenan.

Carrageenans are commonly used in the food and pharmaceutical industry as thickening agents and/or gelation agents. As carrageenans are hydrated within an aqueous composition, they begin to swell, raising the viscosity of the composition exponentially as a function of the total carrageenan concentration. However, the rate of exponential growth is inversely proportional to the sulfate content within each form of carrageenan, so kappa-carrageenan causes a greater exponential growth in viscosity than iota-carrageenan, which itself has a greater effect on viscosity than lambda-carrageenan. Furthermore, heated compositions comprising kappa-carrageenan and iota-carrageenan are able to form gel networks upon cooling, as the polysaccharides form double-helical, quasi-crystalline networks, particularly in the presence of cations. However, the presence of lambda-carrageenan within a composition partially inhibits the formation of a gel, and in compositions where the lambda-carrageenan is the most abundant, gel formation is pre-empted completely. Without being limited by a particular theory, it is believed that the lack of a 3,6-AG group within lambda-carrageenan drives gel inhibition.

Although the relative effects of kappa-, iota-, lambda-forms of carrageenan on the viscosity of a composition are known, the rate of exponential growth of viscosity is generally not predictable from one composition to another, especially where the ratio of kappa-, iota-, and lambda-carrageenans differ between compositions. Additionally, the methods in which the carrageenans and other components are processed also have a dramatic effect on the viscosity of the resulting composition. Factors relevant in the viscosity of the final product include, but are not limited to: heating temperature(s), shear conditions, rotor type, mixing speed, mixing times, and additional components that are also added to the composition. Consequently, the viscosity as a function of total carrageenan concentration can only be modeled where the ratio of each form of carrageenan is constant, and the processing steps are otherwise identical.

While carrageenan compositions that predominantly contain kappa- and iota-forms of carrageenan are useful for thickening compositions or gels, they are inactive against HPV. The lambda-carrageenan form, on the other hand, has been shown to be active against HPV both in vitro (see Buck, et al., above) and in vivo. Several patents and patent publications similarly discuss the use of carrageenan within medicaments as an antimicrobial or antiviral compound (see U.S. Pat. Nos. 5,208,031 and 8,367,098, and U.S. Pat. Pubs. 2005/0171053, 2005/0239742, 2005/0261240, 2006/0127340, 2008/0227749, 2009/0088405, and 2011/0229446, the disclosures of which are incorporated by reference in their entireties). Without being bound by any particular theory, lambda-carrageenan utilizes a "lock and key" type mechanism by which the polysaccharide attracts a virus, interacts with viral capsid, arrests or prevents viral replication, and further inhibits viral activity. This results in significant reduction of the transmission and persistence of viruses, particularly HPV in sexually active men and women.

In one study, a lambda-carrageenan-containing gel was given to sexually-active women that were at high risk of contracting and/or transmitting HPV during sexual activity (see Marais, D., et al., (2011) *Antiviral Therapy* 16:1219-1226, as well as U.S. Pat. No. 8,367,098, the disclosures of which are incorporated by reference in their entireties). The tested composition, Carraguard®, comprises a 3% by weight mixture of kappa-carrageenan and lambda-carrageenan, and has a viscosity of between 30,000 and 40,000 cP. Study participants were instructed to apply the gel in conjunction with vaginal intercourse. Over the three-year period of the study, the authors determined that of the women with "relatively high adherence to gel use," women who were given the lambda-carrageenan-containing gel were only 62% as likely to be classified as HPV positive, relative to the placebo group.

As described above, however, carrageenans (of any form) have historically been used as thickening agents and generally are not preferred in personal lubricant formulations because they cause an exponential increase in the viscosity of the composition. In particular, gel compositions comprising kappa-carrageenan and/or large amounts of iota-carrageenan are typically very viscous and tend to dry out quickly once applied to the skin or epithelial tissue, causing them to form sticky residues and lose their lubricity. As a result, most topical carrageenan-containing compositions, including the one studied in Marais, et al. as well as the related composition in U.S. Pat. No. 8,367,098, are typically gels or creams. To put the viscosity of these carrageenan-containing compositions into context, the viscosity of Carraguard® compared to several common compositions is shown in Table 1, below.

TABLE 1

Approximate Viscosities of Common Materials at Room Temperature

| Material | Viscosity in Centipoise |
| --- | --- |
| Water | 1 cP |
| Milk | 3 cP |
| SAE 10 Motor Oil | 85-140 cP |
| SAE 20 Motor Oil | 140-420 cP |
| SAE 30 Motor Oil | 420-650 cP |
| SAE 40 Motor Oil | 650-900 cP |
| Castrol Oil | 1,000 cP |
| Karo Syrup | 5,000 cP |
| Honey | 10,000 cP |
| Chocolate | 25,000 cP |
| Carraguard ® | 30,000-40,000 cP |
| Ketchup | 50,000 cP |
| Mustard | 70,000 cP |
| Sour Cream | 100,000 cP |

As illustrated in Table 1, the viscosity of the Carraguard® gel utilized in the Marais study is in a range between the viscosity of chocolate and the viscosity of ketchup. Although chocolate and ketchup both have shear-thinning properties, and chocolate in particular can comprise edible compositions that can be utilized during sexual activity, the high viscosity of both compositions causes them to perform poorly as personal and sexual lubricants.

In contrast, compositions that are commonly used as personal lubricants and don't contain carrageenan are typically five to ten times less viscous than the gels used in the Marais study and described in the '098 patent. Ideally, a personal lubricant composition should have a viscosity such that it can be poured or lightly squeezed from its container, remain on the skin after being applied, and undergo shear thinning in response to a stress, such as during sexual activity. Materials commonly found in personal lubricants include, but are not limited to: oils, particularly silicone oils, gums, celluloses, glycerins, polyols, glycols, glycans, polyquaterniums, and other polymers. However, while these lubricants do provide pleasing results during sexual activity, they do not provide any protection against HPV.

Another human in vivo study (see Magnan, et al., above) did explore the use of a less viscous personal composition containing lambda-carrageenan for anti-HPV activity. Similar to the Marais study above, women were randomly assigned a placebo or a commercial composition, Divine 9®, that comprises lambda-carrageenan, and were told to apply the composition in conjunction with sexual activity. The test composition comprised 1.4% by weight of a carrageenan mixture comprising lambda-carrageenan and iota-carrageenan, 37% by weight of propylene glycol, and a viscosity between 1,000 and 4,000 cP (see Example 1, below). Although the Magnan study showed a similar reduction in HPV incidence as the Marais study, the presence of such a high concentration of propylene glycol caused the composition to have an osmolality of over 5,000 mOsm/kg, a level that is potentially dangerous to people who use the composition and which may, for some people, increase the possibility of contracting HPV.

According to results presented in a World Health Organization (WHO) report on sexual health (see "Use and Procurement of Additional Lubricants for Male and Female Condoms: WHO/UNFPA/FHI360 Advisory Note" World Health Organization, Geneva Switzerland, (2012), incorporated by reference in its entirety), research suggests that lubricants with high osmolality might cause vaginal and anal epithelial damage, which could in turn increase the risk of infection by HPV, HIV, and other sexually transmitted infections. The WHO also found that the primary factor that determines the osmolality of a given personal lubricant is the presence of glycols within the composition. Glycols, also commonly known as "polyols," most commonly comprise glycerol, 1,2-propanediol, and 1,3-propanediol, and can upset the water-electrolyte balance within epithelial cells. The WHO goes on to show that most of the commercially available lubricants have osmolalities that far exceed the osmolality of normal vaginal secretions (260-290 mOsmol/kg) and semen (250-380 mOsmol/kg), and recommends that companies tailor the osmolality of their marketed personal lubricant compositions to be under 1,200 mOsmol/kg, with a goal of being as isosmolal as possible with vaginal secretions and/or semen (between 250 and 400 mOsmol/kg).

Antiviral Lubricous Compositions of the Present Invention

The present invention provides several novel antiviral lubricous compositions that comprise lambda-carrageenan, are active against viruses, including HPV, and have a viscosity similar to commonly-available lubricants that do not contain carrageenan. In another embodiment, the antiviral lubricous compositions possess a rheological profile that enable to compositions to retain their moisture and lubricity for several hours upon being applied, and which provide a pleasing experience to people engaging in sexual activity. In further embodiments, the antiviral lubricant compositions are pseudoplastic, non-Newtonian fluid compositions that undergo shear thinning in response to mechanical strain, particularly during sexual activity. In even further embodiments, antiviral lubricant compositions of the present invention can be poured directly from a container, without having to be squeezed or otherwise manually extracted from the container. In other even further embodiments, the antiviral lubricous composition is substantially free of a gel network.

As described above, carrageenans of all types can be obtained from sea algae extracts, typically as a mixture of two, three, or more forms of carrageenan. Carrageenan mixtures can be obtained as raw extracts, or they can be obtained as powders. In further embodiments, carrageenans utilized within antiviral lubricous composition are obtained as a carrageenan powder. Non-limiting examples of commercially-available carrageenan powders include Viscarin® PC 109, Viscarin® PC 209, Viscarin® PC 515, Gelcarin® PC 379, and Gelcarin® PC 911. In even further embodiments, the carrageenan powder is Viscarin® PC 209.

In another embodiment, the carrageenan powder comprises at least about 85% by weight lambda-carrageenan, including at least about 90% by weight of lambda-carrageenan.

In another embodiment, kappa-carrageenan and iota-carrageenan together can comprise up to about 20% by weight of the carrageenan powder including up to about 15%, 10%, 8%, 6%, 4%, 2%, or up to about 1% by weight of the carrageenan powder. In other embodiments, when present, kappa-carrageenan and iota-carrageenan together comprise at least about 1% by weight of the carrageenan powder, including at least about 2%, 4%, 6%, 8%, or 10% by weight, up to at least about 15% by weight, of the carrageenan powder.

In another embodiment, the carrageenan powder comprises at least about 90% by weight lambda-carrageenan and up to about 10% by weight iota-carrageenan. In further embodiments, the carrageenan powder comprises about 90% by weight lambda-carrageenan and about 10% by weight iota-carrageenan.

In another embodiment, the carrageenan powder comprises at least about 90% by weight lambda-carrageenan and up to about 10% by weight kappa-carrageenan. In further embodiments, the carrageenan powder comprises about 90% by weight lambda-carrageenan and about 10% by weight kappa-carrageenan.

In another embodiment, carrageenan mixtures comprising lambda-carrageenan are substantially homogenized within the antiviral lubricous composition, wherein a majority of the carrageenan polysaccharides within the composition are present as free molecules within an aqueous solvent. In further embodiments, the carrageenan mixtures are fully homogenized within the antiviral lubricous composition. In some even further embodiments, homogeneous antiviral lubricous compositions have a substantially uniform appearance and density. In other even further embodiments, the antiviral lubricous composition is a solution in which the ratio of carrageenan to the solvent is substantially uniform. In still other even further embodiments, the antiviral lubricous composition is substantially free of particulates, aggregates, clumps, or other solids that are visible either to the naked eye and/or under 10× magnification under a microscope. In still further embodiments, the antiviral lubricous composition is translucent. In even still further embodiments, the antiviral lubricous composition is transparent.

In another embodiment, carrageenan comprises at least about 0.001% by weight of the antiviral lubricous composition, including at least about 0.01, 0.1, 0.5, 1, 2, 2.5, or 3% by weight, up to at least about 5% by weight of the antiviral lubricous composition. In further embodiments, carrageenan comprises 0.5% to about 2.3% by weight of the antiviral lubricous composition. In even further embodiments, carrageenan comprises 0.8% to about 2.0% by weight of the antiviral composition. In still further embodiments, carrageenan comprises 1.5% to about 1.7% by weight of the antiviral lubricous composition.

Similarly, the viscosity, rheology, sensation, and overall performance of the lambda-carrageenan-containing, antiviral lubricous composition can be controlled by the addition of a minor concentration of a polymer, particularly a polyol, to the antiviral lubricous composition. As described above, polyols are one class of compounds that are commonly found in commercially-available products as bulking agents, flavor retainers/maskers, humectants, stabilizers, anti-crystallizing agents, and for systemic and oral health benefits. Although polyols are typically added to enhance the solubility of other polymers that might be present in commercial personal lubricant products, polyols can also be added in small quantities to antiviral lubricous compositions of the present invention to decrease the viscosity, reduce irritation, provide a secondary source of lubricity, and/or to provide a stimulating "warming" or "tingling" feeling that is often pleasing to the user during sexual activity.

Non-limiting examples of polyols that can be added can include: glycerol; propylene glycol (1,2-propanediol); 1,3-propanediol; 1,3-butanediol; 1,4-butanediol; 2,3-butanediol; xylitol; sorbitol; erythritol; isomalt; lactitol; maltitol; mannitol; polyethylene glycol; and polypropylene glycol; including combinations thereof. Generally, the identity and concentration of the polyol(s) included in an antiviral lubricous composition can be controlled to obtain a desired property. For example, mannitol and xylitol are regulated as food additives for special dietary needs, while polyols are otherwise 'generally regarded as safe' (GRAS). Xylitol also has been used for oral cavity prevention, and mannitol has also been used as a preventative for urinary tract infections. 1,3-butanediol, 1,4-butanediol, 2,3-butanediol, has been shown to reduce irritation in topical application of ointment, cream, and gel compositions. Sugar-based polyols can provide some sweetness, while maltitol can mimic fat textures in edible products.

In another embodiment, the polyol can comprise less than about 50% by weight of the antiviral lubricous composition, including less than about 25, 15, 10, 9, 8, 7, 6, 5, 4, 3, or 2% by weight, down to less than about 1% by weight of the antiviral lubricous composition. In other further embodiments, the antiviral lubricous composition comprises at least about 1% by weight of the polyol, including at least about 2, 3, 4, 5, 6, 7, 8, 9, 10, 15, or 25% by weight, including at least about 35% by weight. In even further embodiments, the polyol comprises about to about 10% by weight of the antiviral lubricous composition.

In another embodiment, the polyol is propylene glycol (1,2-propanediol). In further embodiments, the antiviral lubricous composition comprises up to 8% by weight of propylene glycol. In even further embodiments, the antiviral lubricous composition comprises 0.5% to about 5% by weight of propylene glycol. In still further embodiments, the antiviral lubricous composition comprises about 4% to about 5% by weight of propylene glycol. In some embodiments, the antiviral lubricous composition comprises between about 4.0% and about 4.5% by weight of propylene glycol. In yet still further embodiments, the antiviral lubricous composition comprises between about 2.0% and about 2.5% by weight of propylene glycol.

In another embodiment, the presence of a polyol results an antiviral lubricous composition that is superior to known personal lubricant compositions because it maintains all of the sexual performance benefits of the commercially-available personal lubricants, while also having the ability to inhibit the transmission and/or persistence of HPV. Additionally, the antiviral lubricous compositions are thin enough to provide the tactile benefits of a personal lubricant composition, while also thick enough to remain on the skin or epithelial tissue, particularly the vagina, anus, penis, or mouth prior to initiating sexual contact. In some embodiments, the personal lubricant composition has a viscosity of less than about 10,000 cP, including less than about 8,000, 6,000, 4,000, or 2,000 cP, down to less than about 1,000 cP. In other embodiments, the antiviral lubricous composition has a viscosity of at least about 500 cP, including at least about 1,000, 2,000, 4,000, or 6,000 cP, up to at least about 8,000 cP. In further embodiments, the antiviral lubricous composition has a viscosity of about 500 cP to about 8,000 cP, particularly about 1,000 cP to about 4,000 cP, and more particularly about 2,000 cP to about 3,000 cP. In some embodiments, the antiviral lubricous composition has a viscosity between about 1,500 cP and 2,500 cP. In some embodiments, the antiviral lubricous composition has a viscosity of about 2,000 cP.

In another embodiment, the amount of polyol within the antiviral lubricous composition is limited, in order to provide an osmolality that is within WHO-recommended levels. In other embodiments, the antiviral lubricous composition has an osmolality that is less than about 1,200 mOsm/kg, including less than about 1000, 900, 800, 700, 600, 500, 400, 300, or 200 mOsmol/kg, down to less than about 100 mOsmol/kg. In further embodiments, the osmolality of the antiviral lubricous composition is about 250 to about 800 mOsmol/kg. In other further embodiments, the osmolality of the antiviral lubricous composition is about 650 to about 850 mOsmol/kg.

In another embodiment, the osmolality of the antiviral lubricous composition is isosmolal with the osmolality of human plasma. In further embodiments, the antiviral lubricous composition is isosmolal with semen. In other further embodiments, the antiviral lubricous composition is isosmolal with vaginal secretions. In still other further embodiments, the osmolality of the antiviral lubricous composition is about 250 mOsmol/kg to about 400 mOsmol/kg.

Additionally, and in another embodiment, several supplemental components can be added to the antiviral lubricous composition to complement the antiviral activity of the composition and/or to enhance the composition's performance during sex. In some embodiments, the pH of the antiviral lubricous composition can be controlled by the addition of a pH-adjusting agent. Typically, the pH of the composition once carrageenan is solubilized into water is around 7 to 9. However, the effectiveness of the antiviral lubricous composition can be supplemented by controlling the pH of the composition to either match or be similar to the target surface to which the composition is applied. For instance, the pH of a healthy vagina typically ranges from about 3.5 to about 5.5, whereas the pH of other epithelial cells, including those located within the rectum, is closer to a neutral pH. Thus, in some embodiments, the pH-adjusting agent is an acid that is capable of reducing the pH to a range that is complementary to the intended epithelial surface, particularly below a pH of about 8.0, including less than about 7.0, 6.5, 6.0, 5.5, 5.0, 4.5, or 4.0, down to less than about 3.5. In other embodiments, the pH of the antiviral lubricous composition is at least about 3.5, including at least about 4.0, 4.5, 5.0, 5.5, 6.0, 6.5, or 7.0, up to at least about 8.0. In further embodiments, the pH of the antiviral lubricous composition is about 3.5 to about 5.5, particularly about 4.5. In other further embodiments, the pH of the antiviral lubricous composition is about 5.5 to about 7.0. In still other further embodiments, the pH of the antiviral lubricous composition is about 6.25 to about 6.75.

In some embodiments, the pH-adjusting agent is a strong acid, including, but not limited to, hydrochloric acid or sulfuric acid. However, in other embodiments, the pH-adjusting agent is a weak acid, in order to create a buffered antiviral lubricous composition. Weak acids can be selected based on their buffering capacity, pKa, and availability. Non-limiting examples of weak acids that can be utilized as pH-adjusting agents can include citric acid, lactic acid, and acetic acid. In further embodiments, the antiviral lubricous composition comprises between about 0.01% and about 1.0% by weight of a pH-adjusting agent, particularly between about 0.04% and about 0.06% by weight of the pH-adjusting agent. In even further embodiments, the pH-adjusting agent is citric acid.

In some embodiments, the antiviral lubricous composition can optionally further comprise one or more preservatives, which can be added to prevent microbial growth within the antiviral lubricous composition during storage. Any one or more of several preservatives may be selected from preservatives known to those of skilled in the art, including but not limiting to one or more of the following: methylparaben, benzoic acid, salicylic acid, sorbic acid, propylparaben, and sodium dehydroacetate, including combinations thereof. The preservative may be present in the compositions of this invention in an amount of up to about 1% by weight of the composition.

In some embodiments, the antiviral lubricous composition can optionally further comprise one or more sweeteners that enhance the flavor the composition when it comes in contact with a person's mouth. In some embodiments, the sweetener is an artificial sweetener, the presence of which can also inhibit bacterial growth within the antiviral lubricous composition during storage. Non-limiting examples of artificial sweeteners include, but are not limited to aspartame, saccharin, sucralose, neotame, and acesulfame potassium. In further embodiments, the sweetener is saccharin. In even further embodiments, the antiviral lubricous composition further comprises up to about 0.005% by weight of saccharin. In still further embodiments, the antiviral lubricous composition comprises about 0.125% saccharin.

In addition to or in lieu of sweeteners, the antiviral lubricous composition can optionally further comprise other aromatic agents or fragrances that can mask either the scent of the composition itself or the skin or epithelial tissue to which the antiviral lubricous composition is applied. Non-limiting examples of such fragrances include vanilla, lavender, oregano, thyme, lemongrass, lemons, oranges, anise, cloves, aniseed, cinnamon, geraniums, roses, mint, peppermint, citronella, *eucalyptus*, sandalwood, cedar, rosmarin, pine, vervain fleagrass, or ratanhiae, including combinations thereof, although any essential oil-based fragrance can be chosen. In other embodiments, the antiviral lubricous composition can optionally further comprise one or more chemical, aroma-causing compounds that cause the odor or fragrance within an essential oil-based fragrance. Non-limiting examples of chemical, aroma-causing compounds that can be comprised in any of the antiviral lubricous compositions include carvacrol, eugenol, linalool, thymol, p-cymene, myrcene, borneol, camphor, caryophillin, cinnamaldehyde, geraniol, nerol, citronellol, and menthol, including combinations thereof.

In some embodiments, the antiviral lubricous composition can optionally further comprise one or more metal salts. The addition of a metal salt can have several effects, including controlling the ionic strength of the composition, enhancing its antimicrobial or antiviral activity, or adding in the solubilization of one or more components. Metal salts that can be added include, but are not limited to, zinc, silver, copper, alkali, or alkaline earth metal salts. In further embodiments, the metal salt is a zinc salt or a sodium salt.

In some embodiments, the antiviral lubricous composition can optionally further comprise one or more pharmaceutical antiviral, antifungal, or antimicrobial compounds.

Further, the present invention also provides several methods for reducing, inhibiting, or ameliorating the transmission of a sexually-transmitted virus, including but not limited to HPV, HIV, and HSV, between two or more partners engaging in sexual activity, using the antiviral lubricous compositions made by the processes described below. In a first embodiment, the method comprises the step of contacting the antiviral lubricous composition with the skin or epithelial tissue of one or more of the partners, wherein the skin or epithelial tissue located on or within at least one of the vagina, anus, mouth, or penis. As used herein, the term "vagina" includes skin or epithelial tissue located within the vagina itself and/or surrounding the vagina, including but not limited to the vulva, labia, clitoris, vaginal opening, and the cervix. In further embodiments, at least one partner is male and at least one partner is female. In other further embodiments, at least two partners are male. In still other further embodiments, at least two partners are female.

In another embodiment, the antiviral lubricous composition can be contacted with the skin, particularly skin located on or within at least one of the vagina, anus, mouth, or penis, of one or more of the sexual partners prior to sexual activity, in order to prophylactically inhibit the transmission of a sexually-transmitted virus, including but not limited to HPV, HIV, and HSV, from one sexual partner to another. In such embodiments, the antiviral lubricous composition can be contacted with the skin of one or more of the sexual partners less than about 8 hours, 4 hours, 2 hours, 1 hour, 30 minutes, 15 minutes, 5 minutes, 1 minute, or about 30 seconds prior to sexual activity, down to less than about 1 second prior to sexual activity. In other embodiments, the antiviral lubricous composition can be contacted with the skin of one or more of the sexual partners at least about 30 seconds, 1 minute, 5 minutes, 15 minutes, 30 minutes, 1 hour, 2 hours, 4 hours, or about 8 hours prior to sexual activity.

In another embodiment, the antiviral lubricous composition can be contacted with the skin, particularly skin located on or within at least one of the vagina, anus, mouth, or penis, of one or more of the sexual partners after sexual activity, in order to reduce the spread of a sexually-transmitted virus, including but not limited to HPV, HIV, and HSV, from cell to cell after HPV has been transmitted through skin-to-skin contact. In such embodiments, the antiviral lubricous composition can be contacted with the skin of one or more of the sexual partners less than about 8 hours, 4 hours, 2 hours, 1 hour, 30 minutes, 15 minutes, 5 minutes, 1 minute, or about 30 seconds after sexual activity, down to less than about 1 second after sexual activity. In other embodiments, the antiviral lubricous composition can be contacted with the skin of one or more of the sexual partners at least about 30 seconds, 1 minute, 5 minutes, 15 minutes, 30 minutes, 1 hour, 2 hours, 4 hours, or about 8 hours after sexual activity.

In another embodiment, methods for reducing, inhibiting, or ameliorating the transmission of a sexually-transmitted virus, including but not limited to HPV, HIV, and HSV, between two or more partners engaging in sexual activity further comprise the steps of providing a substrate comprising one or more skin-contacting surfaces, wherein the substrate is configured for insertion into one or more body cavities selected from the group consisting of the vagina, mouth, or anus; lubricating one or more of the skin-contacting surfaces of the substrate with the antiviral lubricous composition, thereby producing a lubricated substrate; contacting the lubricated substrate with the skin or epithelial tissue located on or within at least one of the vagina, anus, mouth, or penis of one or more of the partners; and transferring the antiviral lubricous composition from the lubricated substrate to the skin or epithelial tissue. In some further embodiments, there is only a single person, either a man or a woman, using the substrate during sexual activity. In other further embodiments, there are two or more partners using the substrate, wherein any of the sexual partners can be either a man or a woman.

Substrates suitable for use in conjunction with methods of the present invention include any object, device, or accessory that can be used to contact internal or external surfaces on or within the vagina, anus, mouth, or penis during sexual activity. Non-limiting examples of substrates that can be utilized in accordance with methods of the present invention include condoms; sexual accessory devices such as sex toys, dildos, vibrators, rings, and beads; and internal applicators; comprising materials including but not limited to rubber, latex, plastic, wood, and/or metal. Such examples are described in U.S. Pat. Nos. 6,983,751 and 9,119,763; U.S. Design Pat. No. D599486, and U.S. Patent Publication 2006/0178602, the disclosures of which are included by reference in their entireties. Those skilled in the art would understand that there are countless other examples of substrates, both commercially available and improvised, sexually-themed or not, which can be utilized during sexual activity and to which antiviral lubricous compositions of the present invention can be applied.

In another embodiment, the substrate is a condom. As used in this application, the term "condom," includes devices designed to be worn by either a male or female, within or on the penis, vagina, anus, or finger. Condoms can also be applied over sexual accessory devices, described below. The antiviral lubricous composition can be applied to a skin-contacting surface located on at least one of an internal surface of the condom or an external surface of the condom, either prior to placing the condom on or within the penis, finger(s), vagina, anus, mouth, or other body part or object, or afterward. In further embodiments, a condom pre-lubricated with any of the antiviral lubricous compounds of the present invention can be provided in a packaging that encloses the lubricated condom and seals it from an external environment outside of the packaging. In even further embodiments, the packaging comprises a watertight seal, thereby preventing loss of the antiviral lubricous composition before opening the packaging and applying the pre-lubricated condom over the penis or an analogous sexual accessory device and engaging in sexual activity. Methods for lubricating condoms and packaging them so they are protected from the outside environment prior to use during sexual activity are well known in the art.

In some embodiments in which a condom is a substrate, methods for reducing, inhibiting, ameliorating, or preventing the transmission of a sexually-transmitted virus, including but not limited to HPV, HIV, and HSV, between partners engaging in sexual activity further comprise the steps of: lubricating a skin-contacting surface of a condom; contacting the skin or epithelial tissue within mouth, vagina, or anus of one or more of the partners with the lubricated skin-contacting surface of the condom; and transferring the antiviral lubricous composition from the lubricated skin-contacting surface of the condom to the skin or epithelial tissue.

In further embodiments in which the substrate is a condom, methods for reducing, inhibiting, or ameliorating the transmission of a sexually-transmitted virus, including but not limited to HPV, HIV, and HSV, between two or more partners engaging in sexual activity further comprise the steps of: placing a condom over the finger or penis of one partner; lubricating an external surface of the condom with the antiviral lubricous composition; contacting the skin or epithelial tissue within the mouth, vagina, or anus of one or more additional partners using the lubricated external surface of the condom; and transferring the antiviral lubricous composition from the lubricated external surface of the condom to the skin or epithelial tissue.

In other further embodiments in which the substrate is a condom, methods for reducing, inhibiting, or ameliorating the transmission of a sexually-transmitted virus, including but not limited to HPV, HIV, and HSV, between two or more partners engaging in sexual activity further comprise the steps of: lubricating the condom; sealing the lubricated condom within a packaging; storing the lubricated condom within the packaging; removing the lubricated condom from the packaging; applying the lubricated condom to the finger or penis of one of the sexual partners; contacting the skin or epithelial tissue within the mouth, vagina, or anus of one or more additional partners using the lubricated condom; and transferring the antiviral lubricous composition from the lubricated condom to the skin or epithelial tissue.

In another embodiment, the substrate is an internal applicator. Internal applicators suitable for use in conjunction with methods of the present invention include can any object, device, or accessory that can be configured to be inserted into a person's body cavity and is capable of transferring the antiviral lubricous composition to epithelial tissue within the person's body cavity. Non-limiting examples of internal applicators that can be utilized in accordance with methods of the present invention include syringes, pipettes, swabs, cannulas, elongate sticks or rods, and wearable inserts, comprising materials including but not limited to rubber, latex, plastic, wood, and/or metal. Such examples are described in U.S. Pat. Nos. 2,546,754, 4,557,720, 4,808,166, 6,503,220, 6,537,260, 7,442,179, 7,591,808, 9,290,551, 9,757,549, and 9,884,173, the disclosures of which are included by reference in their entireties. Those skilled in the art would understand that there are countless other examples of internal applicators, both commercially available and improvised, to which antiviral lubricous compositions of the present invention can be applied and can be contacted with the skin or inserted into a body cavity in order to transfer the antiviral lubricous composition to epithelial tissue within the body cavity.

In another embodiment, the internal applicator comprises a skin-contacting surface that is configured to contact epithelial tissue within a person's body cavity, particularly within the vagina or rectum. In other embodiments, the internal applicator comprises a container configured for housing or containing the antiviral lubricous composition prior to transferring the antiviral lubricous composition onto epithelial tissue within a person's body cavity. In either instance, the internal applicator can be provided in a packaging either with or without the antiviral lubricous composition. In further embodiments, the internal applicator is pre-lubricated with the antiviral lubricous composition and sealed within the packaging, protecting the lubricated internal applicator from the external environment and preventing loss of the antiviral lubricous composition before transfer to epithelial tissue within the person's body cavity. Methods for applying lubricants or therapeutic substances to internal applicators and packaging them are well known in the art.

In another embodiment, the present invention also provides methods for reducing, inhibiting, or ameliorating the transmission, symptoms, or effects of a virus, not associated with sexual activity. Methods include the steps of: (a) providing any of the antiviral lubricous compositions above, and (b) contacting the skin or epithelial tissue where a viral infection is known, or is presumed, to be present, either inside or outside the body. The antiviral lubricous composition can be applied to the skin or epithelial tissue using one's finger or any of the applicators described above. In another embodiment, a lubricated swab, stick, or rod can be inserted into any of the body cavities described above, as well as and including the mouth and nose to contact epithelial tissue inside the nasal cavity or throat.

Non-limiting examples of viral taxonomic families that can be treated with any of the antiviral lubricous compositions of the present invention include orthomyxoviridae, paramyxoviridae, pneumoviridae, coronaviridae, retroviridae, herpesviridae, papillomaviridae, picornaviridae, reoviridae, and adenoviridae, andcombinations thereof. Such viruses within these taxonomic families include, but are not limited to: severe acute respiratory disease (SARS) strains 1 and 2 (COVID-19); influenza A, B, and C; enterovirus, rhinovirus, poliovirus, adenovirus, rotavirus and viruses causing measles, mumps, and chicken pox. In another embodiment, the antiviral lubricous composition can be applied to the skin or epithelial of a human having a viral infection, or as prophylaxis to prevent receiving a viral infection. In another embodiment, the antiviral lubricous composition can be applied to the skin or epithelial of an animal having a viral infection, or as prophylaxis to prevent receiving a viral infection.

Processing of the Antiviral Lubricous Compositions

The antiviral lubricous compositions made by processes of the present invention are unique in that they have the ability to inhibit viral activity, including the viral activity of sexually-transmitted viruses such as HPV, HIV, and HSV, and have an optimized viscosity, lubricity, and sensation that enhance their performance as lubricants during sexual activity, while at the same time minimizing the osmolality of the composition. In one embodiment of the invention, the processes to form antiviral lubricous compositions of the present invention can comprise the steps of: (a) providing a carrageenan powder comprising carrageenan, the carrageenan comprising at least about 90% by weight lambda carrageenan and up to about 10% by weight iota carrageenan; (b) combining, while mixing, the carrageenan powder with an aqueous solution comprising a polyol to form a turbid carrageenan suspension; and (c) heating the turbid carrageenan suspension up to a temperature of at least 60° C. and mixing for a time sufficient to transform the turbid carrageenan suspension into a clarified homogeneous solution, thereby forming the antiviral lubricous composition; wherein (i) the antiviral lubricous composition comprises about 0.5% to about 2.3% by weight carrageenan, and up to about 10% by weight polyol; (ii) the antiviral lubricous composition has a viscosity of less than about 5,000 cP; (iii) the antiviral lubricous composition is translucent; and (iv) the antiviral lubricous composition has a turbidity of less than 25 Nephelometric Turbidity Units (NTU).

In another embodiment, processes to form antiviral lubricous compositions of the present invention can additionally comprise a pre-mixing step in which the carrageenan powder and the polyol are first combined to form a wet carrageenan mixture comprising carrageenan and polyol. Without being limited by a particular theory, it is believed that pre-mixing and dispersing the carrageenan powder within the polyol prior to adding water causes the carrageenan polysaccharides to partially unwind, making additional polarizable contacts available to interact upon addition of the aqueous solution. Pre-mixing is believed to have several advantages, including but not limited to: mixing at lower speeds and under lower shear conditions; heating at lower temperatures to homogenize the carrageenan within the aqueous solution; speeding up each mixing step, particularly mixing to homogenize the carrageenan within the aqueous solution; and preserving the carrageenan polysaccharides from breaking into smaller segments, which can negatively affect the viscosity and performance of the composition as a personal lubricant (see below). In further embodiments, processes to form antiviral lubricous compositions of the present invention can comprise the steps of: (a) providing a carrageenan powder comprising carrageenan, the carrageenan comprising at least about 90% by weight lambda-carrageenan and up to about 10% by weight iota-carrageenan; (b) mixing the carrageenan powder with a polyol to form a wet carrageenan mixture, wherein the weight ratio of the glycol to the carrageenan is about 1:1 to about 10:1; (c) combining, while mixing, the wet carrageenan mixture with an aqueous solution to form a turbid carrageenan suspension, wherein the volume ratio of the aqueous solution to the carrageenan is about 45:1 to about 8:1; (d) heating the turbid carrageenan suspension up to a temperature of at least 60° C. and mixing for a time sufficient to transform the turbid carrageenan suspension into a clarified homogeneous solution, thereby forming the antiviral lubricous composition; wherein (i) the antiviral lubricous composition comprises about 0.5% to about 2.3% by weight carrageenan, and up to about 10% by weight polyol; (ii) the antiviral lubricous composition has a viscosity of less than about 5,000 cP; (iii) the antiviral lubricous composition is translucent; and (iv) the antiviral lubricous composition has a turbidity of less than 25 NTU.

In particular, the viscosity of the antiviral lubricous composition is an important factor in its performance as a personal lubricant that can be used in conjunction with sexual activity. Ideally, personal lubricants have a viscosity thick enough to be applied onto the skin or epithelial tissue and remain there until sexual activity is initiated, while also having a rheological profile that the lubricity and moisture from the composition is retained throughout the entire duration of the sexual activity. The presence of carrageenan in a composition is typically antithetical to sexual lubricant performance because the viscosity of the composition exponentially increases as a function of carrageenan concentration (see Example 3, below).

Similarly, the viscosity of the antiviral lubricous composition is sensitive to the balance of several factors in addition to total carrageenan concentration, including but not limited to: the identity and relative concentration of the kappa-, iota-, and lambda-forms of the carrageenan; the concentration and identity of additional components, particularly polyols; and the weight ratio of the carrageenan to the polyol, where the polyol is present. Additionally, the viscosity is also dependent on the processing steps themselves, including but not limited to: the heating of one or more of the wet carrageenan mixture, the carrageenan suspension, and/or the antiviral lubricous composition; the rate of addition of any of the composition components; the rate and duration of any of the mixing steps; and the type of rotor used for mixing. In sum, all the factors above must be tuned to optimize the performance of the antiviral lubricant compositions during sexual activity.

In another embodiment, the viscosity of the antiviral lubricous composition depends not only on the total carrageenan concentration but also the relative concentration of the kappa-, iota-, and lambda-forms of carrageenan differentially affect the rate of exponential growth of the viscosity of the antiviral lubricous composition. As an example, the presence and increasing concentration of kappa-carrageenan causes the steepest increase in the composition's viscosity, whereas the rate of exponential growth caused by the presence and increasing concentration of iota-carrageenan is less than that of kappa-carrageenan, and the rate of exponential growth caused by the presence and increasing concentration of lambda-carrageenan is less than both kappa-carrageenan and iota-carrageenan. Thus, a composition that is predominantly lambda-carrageenan will have a lower viscosity than a composition that is predominantly kappa-carrageenan and/or iota-carrageenan. As a result, and as described above, antiviral lubricous compositions of the present invention can comprise greater than or equal to about 90% lambda-carrageenan and up to about 10% of one or both of kappa-carrageenan or iota-carrageenan. In even further embodiments, the antiviral lubricous compositions comprise about 90% of lambda-carrageenan and about 10% of kappa-carrageenan. In other even further embodiments, the antiviral lubricous compositions comprise about 90% of lambda-carrageenan and about 10% of lambda-carrageenan.

Additionally, the physical form in which carrageenan mixtures are obtained also affects how they must be processed. When carrageenans are obtained as raw extracts, they are already in a predominantly liquid state. However, the shelf life of raw carrageenan extracts is typically reduced relative to solid powders, and carrageenan extracts can include components that are unwanted or even harmful. Consequently, obtaining dried carrageenans in powder form for use in the food or pharmaceutical industry is common, but comes with the trade-off that the carrageenans must be re-solubilized in order to be utilized in a liquid composition.

In applications in which carrageenans are ultimately used as thickening agents, the carrageenan powders can be solubilized simply by high-sheer and high-speed mixing conditions for an extended period of time, often also under aggressive heating conditions. However, carrageenan powders cannot be processed in the same way to produce the antiviral lubricous compositions of the present invention because such conditions cause the resulting compositions to lose their lubricity over time, particularly upon undergoing the shear-thinning stress that occurs during sexual activity. Without being limited by a particular theory, it is believed that the length of the carrageenan polysaccharides is directly correlated with the lubrication and moisture of the resulting composition. As the average length of the polysaccharides increase, the lubricity of the composition also increases. On the other hand, solubilizing carrageenan powders under high-shear and high-stress conditions causes the resulting compositions to prematurely dry out.

In another embodiment, the solubilization of carrageenan powders can be assisted by the addition of the powders to a polyol. As described above, polyols are commonly included in personal lubricant compositions because of the pleasing properties their presence provides during sexual activity. The multiple hydroxyl groups in each polyol molecule have an added benefit because they provide intermolecular contacts with which individual sugars within the larger carrageenan polysaccharide can interact in solution. Without being limited by another theory, it is believed that as the amount of the polyol mixed with the carrageenan powder to form the wet carrageenan mixture increases, the number of polar functional groups within each carrageenan polysaccharide that becomes available to interact with and solubilize within the aqueous solvent also increases, causing a concurrent increase in the viscosity of the antiviral lubricous composition.

Previous antiviral lubricous compositions that include a polyol in conjunction with a lambda-carrageenan lubricant composition have been synthesized by simply adding the carrageenan powder to a bulk solvent that included over 37% by weight of propylene glycol (see Example 1, below). At these concentrations, the propylene glycol concentration causes an unsafe increase in the osmolality of the composition. However, it was determined that simply reducing the polyol concentration within the solvent did not permit the complete homogenization of the carrageenan powder, even with heating up to 75° C. Instead, a plurality of "hydro-sealed" clumps containing dry carrageenan powder surrounded by semi-hydrated carrageenan molecules that were impenetrable to the addition of water were formed. A similar phenomenon was observed in the '098 patent (described above), even with dry powders that were merely exposed to water-containing atmospheric conditions.

In some embodiments, processes to form the antiviral lubricous compositions of the present invention can include a step of first mixing carrageenan powders with at least one polyol to form a wet carrageenan mixture, prior to the addition of the carrageenans. In further embodiments, first solubilizing the carrageenan powder into the polyol facilitates the complete homogenization of the carrageenan polysaccharides within the antiviral lubricous composition.

Additionally, the identity of the polyol and the weight ratio of the polyol to carrageenan also has an effect on the viscosity of the antiviral lubricous composition. As a non-limiting example, 1,2-propanediol is approximately 50 times more viscous than water, but glycerol is approximately 23 times more viscous than 1,2-propanediol. Thus, an antiviral lubricous composition can comprise a much greater concentration of 1,2-propanediol than a second composition comprising glycerol, while having the same viscosity. As a result and in another embodiment, the weight ratio of the polyol to the carrageenan within the wet carrageenan mixture is at least 1:10, including at least 1:5, 1:1, 2:1, 4:1, 6:1, 8:1, 10:1, 20:1, 30:1, or 40:1, up to at least 50:1. In further embodiments, the weight ratio of the polyol to the carrageenan is about 1:1 to about 10:1. In even further embodiments, the polyol is 1,2-propanediol.

Similarly, the weight ratio of the aqueous solution mixed with the wet carrageenan mixture to form the carrageenan suspension also affects the viscosity of the antiviral lubricous composition. In some embodiments, as the weight ratio of the aqueous solution relative to the wet carrageenan mixture increases, the viscosity of the antiviral lubricous composition decreases. In further embodiments, the weight ratio of the aqueous solution mixed with the wet carrageenan mixture to form the carrageenan suspension is about 3:1 to about 60:1. In even further embodiments, the weight ratio of the aqueous solution mixed with the wet carrageenan mixture to form the carrageenan suspension is about 8:1 to about 45:1.

In another embodiment, heating one or more of the wet carrageenan mixture, the carrageenan suspension, and/or the antiviral lubricous composition enables the solubilization and homogenization of the carrageenans in water. Without being limited by a particular theory, it is believed that heating the carrageenans causes at least a partial unfolding of each carrageenan polysaccharide as well as a disruption of intermolecular interactions between polysaccharides, both of which increases the viscosity of the composition. As heating continues, the carrageenan polysaccharides begin to solubilize within the aqueous solution, decreasing the viscosity and forming a homogenous antiviral lubricous composition. However, if the composition continues to be heated after all of the carrageenans have been homogenized, the viscosity of the composition can continue to decrease, and the polysaccharides themselves can dissociate into smaller and smaller oligosaccharides that have lower molecular weights and chain lengths. In further embodiments, the carrageenan suspension is heated until an antiviral lubricous composition is formed that has a viscosity of less than about 5,000 cP. In even further embodiments, the carrageenan suspension is heated until an antiviral lubricous composition is formed that has a viscosity of about 1,000 cP to about 4,000 cP.

Compositions comprising carrageenans, such as the carrageenan suspension, that have not been homogenized are typically cloudy, hazy, or turbid, comprising large numbers of carrageenan particles that are visible by the naked eye. Without being limited by a particular theory, it is believed that the turbidity of the carrageenan suspension results from aggregate formation between two or more carrageenan polysaccharides before they have been fully unwound and exposed to the aqueous solvent. In another embodiment, the carrageenan suspension is heated until a translucent antiviral lubricous composition is formed. In further embodiments the carrageenan suspension is heated until a transparent antiviral lubricous composition is formed. Within such embodiments, the translucent and/or transparent properties of the antiviral lubricous composition is maintained even after packaging and/or storage for an extended period of time. In even further embodiments, there are substantially zero particulates, aggregates, or agglomerates that are visible within the antiviral lubricous composition. In still further embodiments, the fully homogenized antiviral lubricous composition is a solution.

The turbidity of any of the mixtures, suspensions, or antiviral lubricous compositions disclosed herein can be described quantitatively based on the method of determining the concentration of suspended particles in the sample, including but not limited to: Formazin Nephelometric Units (FNU), Jackson Turbidity Units (JTU), NTU, optical density, Helms Units, parts per million (PPM), and others. FNU and NTU are widely used to describe the turbidity of compositions having a uniform distribution of small particles, and are determined by measuring the amount of light that is scattered at 90 degrees relative to an incident light beam. In particular, NTU is measured using visible light as the incident light beam, typically between about 400 nm and about 680 nm, whereas FNU is measured using infrared light as the incident light beam, typically between about 780 nm and about 900 nm.

In another embodiment, the turbidity of any of the mixtures, suspensions, or antiviral lubricous compositions described herein are characterized as a function of NTU. In even further embodiments, the turbidity of the carrageenan suspension upon the addition of carrageenan to the aqueous solution is at least about 100 NTU, including at least about 200, 300, 400, 500, 600, 700, 800, 900, 1000, 2000, or 3000 NTU, up to at least about 4000 NTU. In other even further embodiments, the turbidity of the homogenized antiviral lubricous composition is less than about 25 NTU, including less than about 20, 15, 10, 8, 6, 5, 4, 3, or 2 NTU, down to less than about 1 NTU. In still further embodiments, the turbidity of the homogenized antiviral lubricous composition is less than or equal to about 5 NTU.

In other embodiments, antiviral lubricous compositions, particularly antiviral lubricous compositions that can come in contact with the mouth during sexual activity, made by processes of the present invention can be homogenized until it has a turbidity that is approximately equal to the turbidity of drinking water. Governments, health organizations, and other regulatory bodies have described safety standards to protect people and animals from potentially dangerous health conditions from agents that increase the turbidity of a solution, including but not limited to: polymers and other macromolecules; insoluble small molecules; and bacteria and other microorganisms. The WHO has determined that drinking water should not be more than 5 NTU, and should ideally be below 1 NTU. In the United States, systems that utilize conventional or direct filtration methods must decrease the turbidity of drinking water to less than 1 NTU, and several localities strive to achieve turbidity levels less than 0.1 NTU.

In another embodiment, the type of mixing apparatus, the rotational speed, and the mixing time can be optimized to control the viscosity of the resulting antiviral lubricous composition, and to disperse and homogenize the carrageenan into the aqueous solution. In some embodiments, mixing can be conducted under low-shear conditions for an extended and sufficient time to homogenize the composition, while preserving the length of each carrageenan polysaccharide and maintaining their lubricity prior to applying the composition to the skin or epithelial tissue, particularly before or in conjunction with sexual activity. In contrast and in other embodiments, mixing can be conducted under high-shear conditions for a minimum period of time, but mixing beyond a minimum time can irreparably disrupt the carrageenan polysaccharides, decrease the viscosity of the composition, and diminish the composition's performance as a lubricant during sexual activity. Non-examples of mixers include, but are not limited to, screw mixers, tumble mixers, ribbon mixers, and paddle mixers. In even further embodiments, a paddle mixer can be used for each of the mixing steps for forming the antiviral lubricous composition. Similarly, mixing at relatively low speeds also preserves the structural integrity of each polysaccharide. In other even further embodiments, each of the mixing steps is conducted with a mixing speed of equal or less than about 500 RPM. In still further embodiments, mixing of the antiviral lubricous composition after homogenizing the carrageenan within the aqueous solution can occur at speeds less than or equal to about 250 RPM.

In another embodiment, processes for forming the antiviral lubricous composition can further comprise several steps, including: (e) cooling the homogenized antiviral lubricous composition until the temperature of the antiviral lubricous composition is less than about 30° C.; (f) mixing one or more pH-adjusting agents into the cooled antiviral lubricous composition, at a weight sufficient to adjust the antiviral lubricous composition to a pH of about 3.5 to about 7.0; (g) optionally mixing one or more sweeteners into the carrageenan suspension or the cooled antiviral lubricous composition, at up to 0.5% by weight of the antiviral lubricous composition; and (h) optionally mixing one or more preservatives into the carrageenan suspension or the cooled antiviral lubricous composition, at up to 1% by weight of the antiviral lubricous composition. In further embodiments, each of the additional components, such as the pH-adjusting agents, sweeteners, and preservatives described above, as well as salts and/or aromatic agents, can be included within the antiviral lubricant composition to supplement its anti-HPV activity and/or enhance its performance during sexual activity. Composition properties as a result of adding pH-adjusting agents, sweeteners, and preservatives are described above.

In another embodiment, the processes described above can be utilized to homogenize carrageenan mixtures having different lambda-, kappa, and iota-carrageenan ratios into an aqueous solvent at any desired viscosity. In some embodiments, lambda-carrageenan comprises at least about 50% by weight of the carrageenan powder, including at least about 60 or 70% by weight, up to about 80% by weight of the carrageenan powder. In other embodiments, lambda-carrageenan comprises less than about 85, 80, or 70% by weight, down to less than about 60% by weight of the carrageenan powder. Within such embodiments, the amount of kappa- and iota-carrageenans can increase such that when present, kappa-carrageenan and iota-carrageenan together comprise up to about 50% by weight of the carrageenan powder, including up to 40%, 30%, or up to 20% by weight of the carrageenan powder.

While particular embodiments of the invention have been described, the invention can be further modified within the spirit and scope of this disclosure. Those skilled in the art will recognize or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference and shall not be construed as an admission that such reference is available as prior art to the present invention. All of the incorporated publications and patent applications in this specification are indicative of the level of ordinary skill in the art to which this invention pertains and are incorporated to the same extent as if each individual publication or patent application was specifically indicated and individually indicated by reference.

The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

EXAMPLES

The following working and prophetic examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Working Examples

Example 1: Preparation of High-Osmolality Personal Lubricant Composition

The following antiviral lubricous composition was prepared in accordance with the procedure used to make commercial preparations of the lambda-carrageenan-based personal lubricant, Divine 9®.

Ingredients
  55.70% (w/w) deionized water
  37.40% (w/w) propylene glycol
  5.00% (w/w) of 2.5% (w/v) sodium saccharin solution in deionized water
  1.40% (w/w) Viscarin® PC 209 carrageenan powder
  0.04% (w/w) citric acid
  0.01% (w/w) sodium hydroxide
  0.95% (w/w) GeoGard ECT preservative (Lonza Consumer Care)
  0.03% (w/w) GeoGard 111—Sodium Dehydroacetate preservative (Lonza Consumer Care)

All ingredients were combined except the Viscarin® PC 209 carrageenan powder and mixed together thoroughly. With constant mixing, the composition was then gradually heated up to 75° C. When the composition reached 50° C., Viscarin® PC 209 carrageenan powder was gradually combined until all of the carrageenan powder was added. The composition continued to be mixed at 75° C. until all of the Viscarin® PC 209 carrageenan powder was dissolved, about two hours. Upon dissolution of the carrageenan powder, mixing was ceased and the composition was cooled rapidly. Once the temperature of the composition reached 30° C., citric acid was added to bring the pH to about 6.5, +/−0.25.

Example 2: Preparation of a Low-Osmolality Antiviral Lubricous Composition

The following antiviral lubricous composition was prepared in accordance with embodiments of the present invention and the procedure below:

Ingredients
  88.49% (w/w) deionized water
  4.40% (w/w) 1,2-propanediol
  5% (w/w) of 2.5% (w/v) Sodium saccharin solution in deionized water
  1.60% (w/w) Viscarin® PC 209 carrageenan powder
  0.05% (w/w) citric acid 0.32% (w/w) 2-phenoxyethanol
0.11% (w/w) chlorphenesin
0.03% (w/w) GeoGard 111—Sodium Dehydroacetate preservative (Lonza Consumer Care)

The Viscarin® PC 209 carrageenan powder and 1,2-propanediol were mixed for approximately 10 minutes to form a wet carrageenan mixture, using a Mixer Direct R-AD665 industrial gallon paddle mixer with two folding impeller blades, operating at 500 RPM. After 10 minutes, no aggregate particles of powder were observed within the wet carrageenan mixture. With continued mixing, approximately 90% of the volume of the water and all of the saccharin was added to the wet carrageenan mixture over an additional 5 minutes, forming a turbid carrageenan suspension. The carrageenan suspension was heated to 70° C. and allowed to mix under the same mixing conditions until the carrageenan powder was completely homogenized within the water. Homogenization was achieved upon a transition from a turbid suspension into a clarified solution, after about 90 minutes. Mixing continued for 10 more minutes after homogenization took place. The mixer was paused and the composition was cooled to less than 30° C. Once cooled, the preservatives, citric acid, and remaining water were added to the composition, with mixing at 250 RPM for 20 minutes. The resulting antiviral lubricous composition was translucent and has a pH of about 6.5, +/−0.25.

Example 3: Exponential Effect of Carrageenan Concentration on Composition Viscosity In order to evaluate the effect of the carrageenan on the viscosity of antiviral lubricous compositions, several compositions were formulated at varying concentrations of the carrageenan. A first sample, Sample V1, was prepared according the same ingredient specifications and procedure as the composition of Example 1. Additional antiviral lubricous compositions (Samples V2-V5) with different concentrations of carrageenan were prepared, using the procedure of Example 2. The volume of water added was adjusted as necessary. The final volume for each sample composition of 200 mL. The concentration of carrageenan and viscosity of each sample are provided in Table 2, below.

TABLE 2

Measured Viscosities of Antiviral Lubricous Compositions

| Sample Number | Carrageenan powder (w/v) | Measured Viscosity (cP) |
|---|---|---|
| V1 | 1.40 | 1975 |
| V2 | 1.73 | 2900 |
| V3 | 2.10 | 4000 |
| V4 | 2.15 | 4400 |
| V5 | 2.20 | 4750 |

Each of the viscosity measurements were taken using a Brookfield LVF Dial Reading Viscometer, using a #2 spindle at 12 revolutions per minute, according to instructions provided with the instrument. The relationship between the viscosity of the antiviral lubricous composition as a function of the carrageenan concentration is illustrated in FIG. 1. Fitting the data to an exponential model using Microsoft Excel yields a trendline with an $R^2$ value of 0.994, indicating a strong correlation between the data and the model.

Example 4: Linear Effect of 1,2-Propanediol on Composition Osmolality

In order to evaluate the effect of 1,2-propanediol on the osmolality of antiviral lubricous compositions, several compositions were formulated at varying concentrations of the 1,2-propanediol. A first sample, Sample 01, was prepared according the same ingredient specifications and procedure as the composition of Example 1. Additional antiviral lubricous compositions (Samples 02-05) with different concentrations of 1,2-propanediol were prepared, using the procedure of Example 2. The volume of water added was adjusted as necessary. The final volume for each sample composition of 50 mL. The concentration of 1,2-propanediol and osmolality of each sample are provided in Table 3, below.

TABLE 3

Measured Osmolality of Antiviral Lubricous Compositions

| Sample Number | 1,2-propanediol (w/v) | Osmolality (mOsmol/kg) |
|---|---|---|
| 01 | 37.4 | 5300 |
| 02 | 8.8 | 1622 |
| 03 | 6.6 | 1181 |
| 04 | 4.4 | 800 |
| 05 | 4.0 | 730 |

Figure 2:
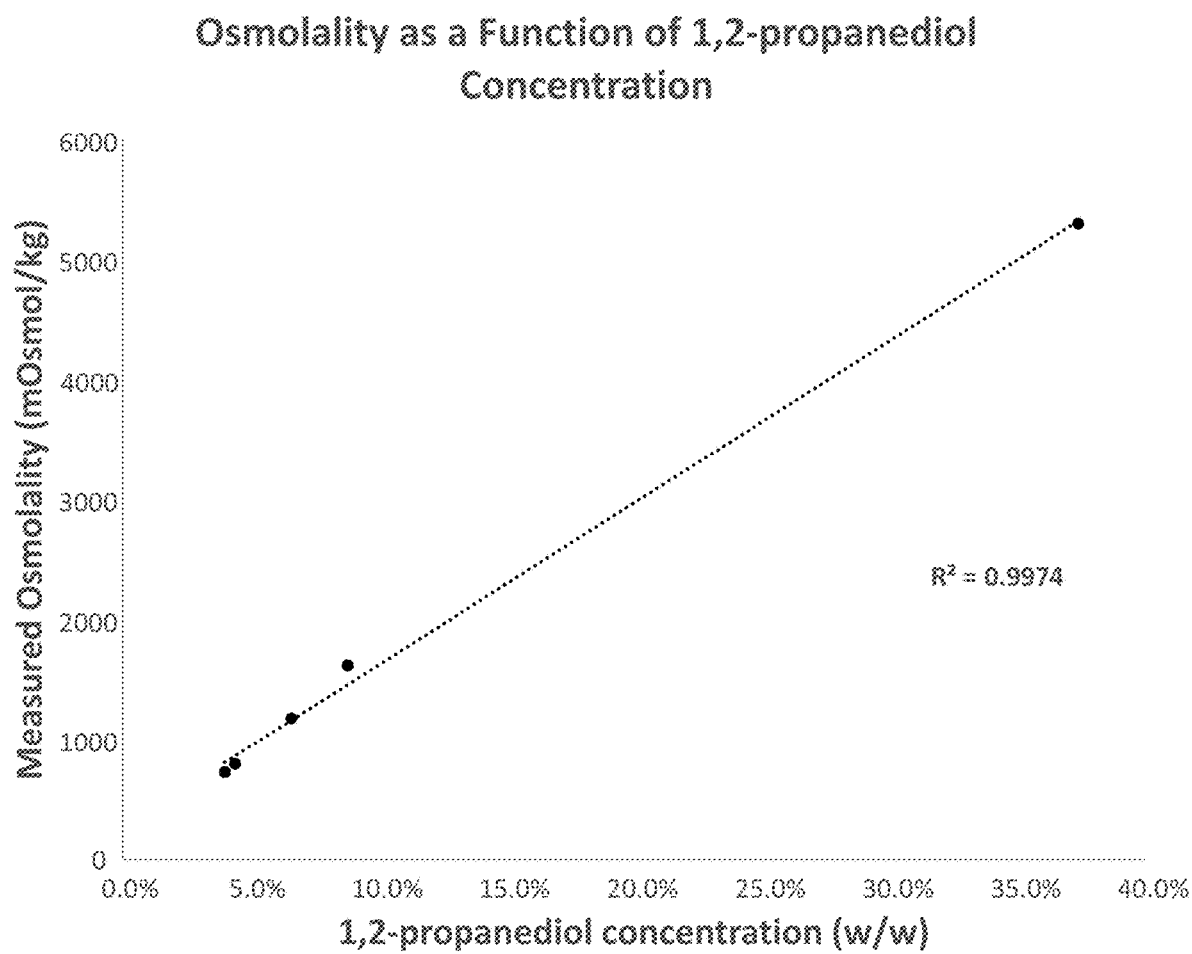
FIG. 2 shows a plot of the osmolality of antiviral lubricous compositions as a function of 1,2-propanediol concentration.

Each of the osmolality measurements were performed with an osmometer capable of measuring freezing point depression, in accordance with United States Pharmacopeial Convention standard protocols (see USP <785>, Osmolality and Osmolarity, 2017). The relationship between the osmolality of the antiviral lubricous composition as a function of the 1,2-propanediol concentration is illustrated in FIG. 2. Fitting the data to a linear model using Microsoft Excel yields a trendline with an $R^2$ value of 0.9974, indicating a strong correlation between the data and the model.

Prophetic Examples

Example 5: Characterization of the Disaccharide Content of Antiviral Lubricous Compositions Each of the primary forms of carrageenan comprises a different repeating disaccharide structure—iota-carrageenan comprises alternating disaccharides of D-galactaose-4-sulfate and 2-sulfo-3,6-anhydro-D-galactose; kappa-carrageenan comprises alternating disaccharides of D-galactose-4-sulfate and 3,6-anyhdro-D-galactose; and lambda-carrageenan comprises alternating disaccharides of D-galactose-2-sulfate (1-3 linked) and D-galactose-2,6-disulfate (1,4 linked). As a result, lambda-carrageenan typically contains more sulfate groups per polymer and substantially fewer anhydrogalactose residues, which are commonly found in iota-carrageenan and kappa-carrageenan. Consequently, the relative ratio of lambda- to iota- to kappa-carrageenan in an antiviral lubricous composition can be determined by several analytical techniques, including but not limited to infrared spectroscopy (IR), nuclear magnetic resonance (NMR) spectroscopy (see de Araujo, C. A., et al., (2013) *Carbohydrate Polymers* 91:483-491, and liquid chromatography coupled to mass spectroscopy (LC-MS) (see Diez, F., et al., (2017) "Development of an Analytical Method to Determine the amount of e Carrageenan in HPMC Capsules by LCMS," American Association of Pharmaceutical Scientists Poster Submission, obtained from the internet at http://abstracts.aaps.org/Verify/AAPS2017/PosterSubmissions/M8109.pdf on May 3, 2018).

In particular, IR spectrum of antiviral lubricous composition can be utilized to determine both a profile of the composition that can be compared against other lambdacarrageenan-containing compositions, as well as a relative molar ratio of the lambda-, iota-, and kappa-carrageenan forms within the composition (see Volery, P., et al., (2004) 1 *Agric. Food Chem.* 52 (25):7457-7463). Within the fingerprint region of a typical IR spectrum (between about 800 $cm^{-1}$ and about 1250 $cm^{-1}$), carrageenan has several strong, broad absorption bands for residues or functional groups commonly found within each polymer, as well as a strong absorption maximum between about 1065 $cm^{-1}$ and about 1020 $cm^{-1}$, particularly about 1050 $cm^{-1}$. The intensity of the absorbance of a particular band corresponding to a residue or functional group, relative to the intensity of the major absorption band at 1050 $cm^{-1}$, can be used to determine the relative abundance of a particular form of carrageenan with the IR sample. Characteristic absorption bands and their intensities relative to the major absorption band at 1050 $cm^{-1}$ are illustrated below in Table 4.

TABLE 4

Common IR absorption bands in carrageenan

| Wave Number ($cm^{-1}$) | Molecular Assignment | Absorbance relative to 1050 $cm^{-1}$ | | |
|---|---|---|---|---|
| | | kappa | iota | lambda |
| 1220-1260 | Ester sulfate | 0.2-1.2 | 1.2-1.6 | 1.4-2.0 |
| 928-933 | 3,6-anydrogalactose | 0.2-0.6 | 0.2-0.4 | 0-0.2 |
| 840-850 | Galactose-4-sulfate | 0.1-0.5 | 0.2-0.4 | — |
| 825-830 | Galactose-2-sulfate | — | — | 0.2-0.4 |
| 810-820 | Galactose-6-sulfate | — | — | 0.1-0.3 |
| 800-805 | 3,6-anhydrogalactose-2-sulfate | 0-0.2 | 0.2-0.4 | — |

A study is conducted in accordance with principles of the present invention to characterize the carrageenan within a sample of the antiviral lubricous composition. A sample of the antiviral lubricous composition is subjected to IR spectroscopic analysis according to the procedure described in the Food and Agricultural Organization of the United Nations/World Health Organization joint compendium of food additive specifications (see "Carrageenan, *Compendium of Food Additive Specifications FAO JEFCA Monographs* 16; FAO/WHO Publications; Rome, Italy; pp. 7-12). It is expected that antiviral lubricous compositions of the present invention possess a unique and characteristic IR spectrum that can be compared against other compositions that contain lambda-carrageenan. It is also expected that the IR spectrum for the antiviral lubricous composition possesses peaks between 810 $cm^{-1}$ and 820 $cm^{-1}$ as well as 825 $cm^{-1}$ and 830 $cm^{-1}$, indicating the presence of lambda-carrageenan within the antiviral lubricous composition. It is further expected that the molar ratio of lambda-carrageenan in the antiviral lubricous composition is greater relative to the molar ratio of kappa-carrageenan and iota-carrageenan.

Example 6: Antiviral Efficacy of the Antiviral Lubricous Composition Against Respiratory Viruses in Human Subjects A study is conducted in accordance with principles of the present invention to determine the efficacy of an antiviral lubricous composition in human subjects who have an active viral respiratory infection, such as COVID-19, or are in close contact with someone who has an active viral respiratory infection. Participants are asked to apply the antiviral lubricous composition of Example 2 to the tip of a swab, and to insert the swab through the nose and until contact is made with epithelial tissue inside the nose and nasal cavity. Alternatively, a participant is asked to dispense a volume of antiviral lubricous composition into the mouth, and to swish, swirl, or gargle the composition within the mouth before swallowing. The volume of the composition administered by either method is between 0.1 mL and 5 mL. The antiviral lubricous composition of Example 2 can be administered in its neat form, or diluted, prior to administration. Participants are asked to administer the antiviral lubricous composition to the nasal cavity 1-4 times a day. Additionally, participants can be asked to administer the composition before and/or after coming into close contact with another person or going out into public. It is expected that for those with an active infection, the progression of symptoms is either abated or reduced until being eliminated completely, on a dose-dependent basis. It is also expected that the viral load of the virus transmitted to subjects who are not sick, but who are in close contact with a sick patient, is either delayed, reduced, or eliminated.

Because the instant application is a continuation or divisional application, to the extent any amendments, characterizations, or other assertions previously made (in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

I claim:

1. An antiviral lubricous composition consisting of:
   (a) from about 0.1% to about 5% by weight of carrageenan;
   (b) from about 0.1% to about 50% by weight of one or more polyols;
   (c) from about 0.01% to about 1% by weight of one or more pH-adjusting agents;
   (d) water; and
   (e) optionally, one or more selected from the group consisting of a sweetener, a preservative, a zinc salt, and a spermicide;
   wherein:
   (i) from about 80% to about 95% by weight of the carrageenan is lambda-carrageenan;
   (ii) from about 5% to about 20% by weight of the carrageenan is one or both of kappa-carrageenan and iota-carrageenan;
   (iii) the one or more polyols are selected from the group consisting of glycerol, propylene glycol, 1,3-propanediol, 1,3-butanediol, 1,4-butanediol, 2,3-butanediol, xylitol sorbitol, erythritol, isomalt, lactitol, maltitol, mannitol polyethylene glycol, polypropylene glycol;
   (iv) the one or more pH-adjusting agents comprise at least one organic acid and its conjugate base;
   (v) the antiviral lubricious composition has a viscosity of from about 500 cP to about 10,000 cP;
   (vi) the antiviral lubricious composition has an osmolality of from about 250 mOsmol/kg up to less than 1,200 mOsmol/kg;
   (vii) the antiviral lubricious composition is an aqueous homogeneous solution having a turbidity less than or equal to about 25 Nephelometric Turbidity Units (NTU); and
   (viii) the pH of the antiviral lubricious composition is from about 3.5 to about 8.0.

2. The antiviral lubricous composition according to claim 1, wherein the pH of the lubricous composition is less than about 7.0.

3. The antiviral lubricous composition according to claim 1, wherein at least about 90% by weight of the carrageenan is lambda-carrageenan.

4. The antiviral lubricous composition according to claim 1, wherein the one or more polyols is solely propylene glycol.

5. The antiviral lubricous composition according to claim 1, wherein the antiviral lubricous composition contains saccharin as the sweetener, and wherein amount of saccharin present in the antiviral lubricous composition is less than 5% by weight.

6. The antiviral lubricous composition according to claim 1, wherein the antiviral lubricous composition contains the preservative, and wherein the amount of the preservative present in the antiviral composition is less than about 1% by weight.

7. The antiviral lubricous composition according to claim 1, wherein the viscosity of the antiviral lubricous composition is at least about 1,000 cP, and up to about 4,000 cP.

8. The antiviral lubricous composition according to claim 1, wherein the antiviral lubricous composition contains at least about 1.5% by weight, and up to about 2.0% by weight, of the carrageenan.

9. The antiviral lubricous composition according to claim 1, wherein the viscosity of the antiviral lubricous composition is at least about 2,000 cP, and up to about 3,000 cP.

10. The antiviral lubricous composition according to claim 1, wherein the antiviral lubricous composition contains at least about 1.5% by weight, and up to about 1.7% by weight, of the carrageenan.

11. The antiviral lubricous composition according to claim 1, wherein the pH of the antiviral lubricous composition is between about 3.5 and about 5.5.

12. The antiviral lubricous composition according to claim 1, wherein the pH of the antiviral lubricous composition is between about 5.5 and about 7.0.

13. The antiviral lubricous composition according to claim 1, wherein the antiviral lubricious composition contains the zinc salt.

14. The antiviral lubricous composition according to claim 6, wherein the preservative is selected from the group consisting of methylparaben, benzoic acid, salicylic acid, sorbic acid, polyparaben, sodium dehydroacetate and combinations thereof.

15. The antiviral lubricous composition according to claim 1, wherein the antiviral lubricious composition contains the spermicide.

16. The antiviral lubricous composition according to claim 1, wherein the antiviral lubricious composition has a viscosity of from about 1,500 cP to about 2,500 cP.

17. The antiviral lubricous composition according to claim 1, wherein the antiviral lubricious composition has a turbidity less than or equal to about 5 Nephelometric Turbidity Units (NTU).

18. The antiviral lubricous composition according to claim 1, wherein the antiviral lubricious composition is transparent, and there are substantially zero particulates, aggregates or agglomerates visible within the antiviral lubricious composition.

19. The antiviral lubricous composition according to claim 1, wherein the at least one organic acid is citric acid and its conjugate base is sodium citrate and/or magnesium citrate.

20. The antiviral lubricous composition according to claim 1, wherein about 0.5% to about 2.3% by weight of the antiviral lubricious composition is carrageenan, wherein the antiviral lubricious composition has a viscosity of less than about 5,000 cP, wherein the antiviral lubricious composition is translucent, and wherein the antiviral lubricious composition has a turbidity of less than about 5 Nephelometric Turbidity Units (NTU).

* * * * *